United States Patent
Saqi et al.

(10) Patent No.: US 9,541,477 B2
(45) Date of Patent: Jan. 10, 2017

(54) MEDICAL APPARATUS AND METHOD FOR COLLECTING BIOLOGICAL SAMPLES

(71) Applicant: The Trustees of Columbia University in the City of New York, New York, NY (US)

(72) Inventors: Anjali Saqi, New York, NY (US); Keith Yeager, Jersey City, NY (US)

(73) Assignee: THE TRUSTEES OF COLUMBIA UNIVERSTIY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 14/256,138

(22) Filed: Apr. 18, 2014

(65) Prior Publication Data

US 2014/0227732 A1    Aug. 14, 2014

Related U.S. Application Data

(63) Continuation of application No. PCT/US2012/060914, filed on Oct. 18, 2012.
(Continued)

(51) Int. Cl.
*G01N 1/31* (2006.01)
*G01N 1/40* (2006.01)
(Continued)

(52) U.S. Cl.
CPC ............. *G01N 1/31* (2013.01); *A61B 10/0283* (2013.01); *B01L 3/5021* (2013.01);
(Continued)

(58) Field of Classification Search
CPC .... G01N 1/31; G01N 1/4077; A61B 10/0283; B01L 3/5021
(Continued)

(56) References Cited

U.S. PATENT DOCUMENTS 4,534,863 A    8/1985   Bacon et al.
4,822,495 A    4/1989   Michels
(Continued)

FOREIGN PATENT DOCUMENTS

JP    2001-296220 A    10/2001
JP    2001-522042 A    11/2001
(Continued)

OTHER PUBLICATIONS

Loukeris, K. et al. "Cytological cell blocks: Predictors of squamous cell carcinoma and adenocarcinoma subtypes." (Nov. 2012) Diagnostic Cytopathology, vol. 40, Issue 5, p. 380-387.
(Continued)

*Primary Examiner* — Jill Warden
*Assistant Examiner* — Jacqueline Brazin
(74) *Attorney, Agent, or Firm* — Reed Smith LLP; Lisa A. Chiarini

(57) ABSTRACT

A medical apparatus and method of preparing one or more cell blocks. The medical apparatus comprises at least one elongate tubular body having a proximal end and a distal end and a filter membrane disposed between the proximal end and a distal end of the elongate tubular body. The filter membrane, which can include alignment features and structural features to engage the tubular body, and/or cover, is sectionable. Additionally, in some embodiments a second elongate tubular body is provided which telescopingly receives at least a portion of the first elongate tubular body. In other embodiments, a support member is provided for engaging the filter membrane and positioning the filter membrane at a midpoint of the elongate tubular body during centrifuging.

26 Claims, 27 Drawing Sheets

Related U.S. Application Data

(60) Provisional application No. 61/548,316, filed on Oct. 18, 2011, provisional application No. 61/657,691, filed on Jun. 8, 2012.

(51) Int. Cl.
*A61B 10/02* (2006.01)
*B01L 3/00* (2006.01)
*G01N 1/36* (2006.01)
*G01N 1/28* (2006.01)

(52) U.S. Cl.
CPC .... *G01N 1/4077* (2013.01); *B01L 2300/0618* (2013.01); *B01L 2300/0681* (2013.01); *G01N 1/36* (2013.01); *G01N 2001/2873* (2013.01); *G01N 2001/4088* (2013.01)

(58) Field of Classification Search
USPC ........................................................ 422/534
See application file for complete search history.

(56) References Cited

U.S. PATENT DOCUMENTS

| | | | |
|---|---|---|---|
| 4,957,637 A | | 9/1990 | Cornell |
| 5,026,638 A | * | 6/1991 | Saperstein ............... C12Q 1/18 435/243 |
| 5,042,502 A | * | 8/1991 | Guirguis ............ A61B 10/0045 422/419 |
| 5,552,325 A | | 9/1996 | Nochumson et al. |
| 5,556,544 A | * | 9/1996 | Didier ................ B01D 33/0158 209/172 |
| 5,578,459 A | * | 11/1996 | Gordon .................... B01J 3/006 135/29 |
| 5,833,860 A | | 11/1998 | Kopaciewicz et al. |
| 5,860,937 A | | 1/1999 | Cohen |
| 5,882,943 A | * | 3/1999 | Aldeen ................... B01L 3/502 210/323.2 |
| 5,948,687 A | * | 9/1999 | Cleator .............. A61B 10/0038 422/408 |
| 6,379,565 B1 | * | 4/2002 | Guirguis ............. G01N 1/2813 210/767 |
| 6,913,921 B2 | | 7/2005 | Fischer |
| 7,179,424 B2 | | 2/2007 | Williamson, IV et al. |
| 7,316,779 B2 | | 1/2008 | Pressman et al. |
| 8,152,738 B2 | | 4/2012 | Li et al. |
| 8,329,120 B2 | | 12/2012 | Williamson, IV et al. |
| 8,383,067 B2 | | 2/2013 | Williamson, IV |
| 8,796,038 B2 | | 8/2014 | Williamson, IV et al. |
| 2002/0098126 A1 | * | 7/2002 | Day ..................... B01L 3/5453 422/550 |
| 2002/0130100 A1 | | 9/2002 | Smith |
| 2002/0192656 A1 | | 12/2002 | Richardson et al. |
| 2003/0215936 A1 | * | 11/2003 | Kallioniemi ............. G01N 1/36 435/287.1 |
| 2004/0121456 A1 | | 6/2004 | Fischer |
| 2004/0137417 A1 | | 7/2004 | Ryan |
| 2006/0037903 A1 | * | 2/2006 | Smith .................. B01L 3/5021 210/240 |
| 2006/0121597 A1 | | 6/2006 | Li |
| 2007/0166834 A1 | | 7/2007 | Williamson, IV et al. |
| 2007/0218542 A1 | | 9/2007 | Li et al. |
| 2008/0097285 A1 | | 4/2008 | Scampini |
| 2010/0248215 A1 | * | 9/2010 | Halverson ................ G01N 1/38 435/5 |
| 2010/0297691 A1 | | 11/2010 | Ribeiro et al. |
| 2014/0205515 A1 | | 7/2014 | Williamson, IV et al. |

FOREIGN PATENT DOCUMENTS

| | | |
|---|---|---|
| JP | 2007-292580 A | 11/2007 |
| WO | WO 95/14533 | 6/1995 |
| WO | 9923468 A1 | 5/1999 |
| WO | 2004/041994 | 5/2004 |
| WO | 2006058078 | 6/2006 |
| WO | 2014081877 | 5/2014 |
| WO | WO2014081877 A1 | 5/2014 |

OTHER PUBLICATIONS

Nathan, N.A. et al. "Cell Block Cytology: Improved Preparation and Its Efficacy in Diagnostic Cytology." (2000) American Society for Clinical Pathology, vol. 114, Issue 4, pp. 599-606.
Nigro, K. et al. "Comparison of Cell Block Preparation Methods for Nongynecologic ThinPrep Specimens" (2007) Diagnostic Cytopathology, vol. 35, Issue 10, pp. 640-643.
Varsegi, G.M. and Shidham, V. "Cell Block Preparation from Cytology Specimen with Predominance of Individually Scattered Cells." (2009)Journal of Visualized Experiments, vol. 26, pp. 1-8.
Yang, G.C. et al. "Compact cell blocks. Use for body fluids, fine needle aspirations and endometrial brush biopsies." (1998) Acta Cytologica, vol. 42, Issue 3, pp. 703-706.
International Search Report PCT/US13/71083, Mar. 21, 2014.
Extended European Search Report mailed May 29, 2015 in corresponding Application No. 12841594.0.
Loukeris, K. et al. "Cytological Cell Blocks: Predictors of Squamous Cell Carcinoma and Adenocarcinoma Subtypes."(2010) Diagonostic Cytopathology, DOI 10.1002/dc.
Rekhtman,N. et al. "Suitability of Thoracic Cytology for New Therapeutic Paradigms in Non-small Cell Lung Carcinoma." (Mar. 2011) Journal of Thoracic Oncology, vol. 6, No. 3.
Rekhtmann, N. et al. "Immunohistochemical algorithm for differentiation of lung adenocarcinoma and squamous cell carcinoma based on large series of whole-tissue sectuibs with validation in small specimens." (2011) Modern Pathology, p. 1-12.
Varsegi et al. "Cell Block Preparation from Cytology Specimen Predominance of Individually Scattered Cells." Journal of Visualized Experiments. 29: 1-7. Jul. 21, 2009.
International Search Report PCT/US12/60914, (Jan. 9, 2013).

* cited by examiner

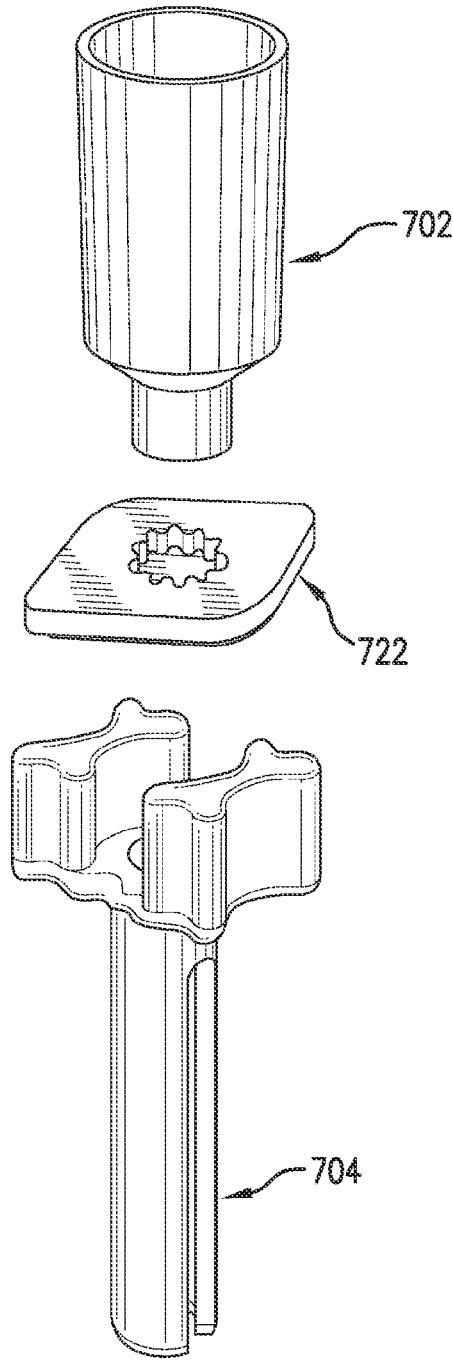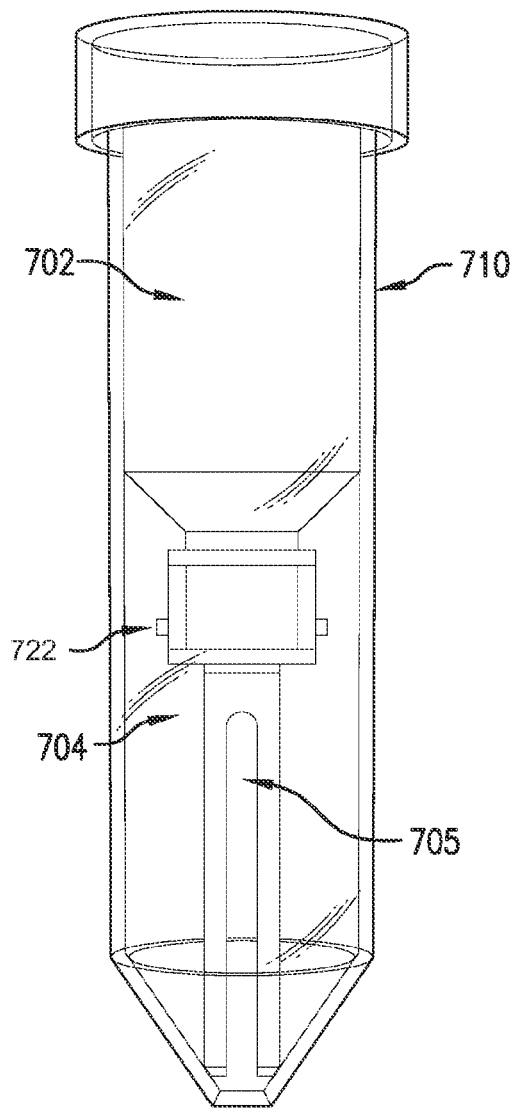
FIG.14A
FIG.14B

MEDICAL APPARATUS AND METHOD FOR COLLECTING BIOLOGICAL SAMPLES

RELATED APPLICATIONS

This application is a Continuation of PCT/US 12/60914, filed Oct. 18, 2012, which claims priority to the benefit of the filing date of U.S. Provisional Patent Application No. 61/548,316 filed Oct. 18, 2011 and 61/657,691 filed Jun. 8, 2012; these applications are hereby incorporated by reference in their entirety.

FIELD

The disclosed subject matter relates to a system and method for preparing cells for diagnostic tests and procedures. Particularly, the disclosed subject matter relates to a cell block apparatus and methods for preparing a cell block.

BACKGROUND

Medicine is becoming less invasive and more personalized. For example, a patient presenting with a mass in the lung or pancreas is not necessarily scheduled for surgery to characterize the lesion as neoplastic or not. Instead, a minute sample of cells from the lesion is obtained through a procedure called a fine needle aspiration (FNA), which involves aspirating cells with a small needle after it is localized to the site of interest with the aid of CT scan and/or ultrasound. When performing FNA, either no incision is made, or the biopsy site is inconspicuous, similar to a puncture wound following a blood draw, which allows for outpatient procedures and prevents need for hospitalization. By examining cells under a microscope, pathologists render diagnoses of benignity or malignancy. At one time, there were limited tumor and therapeutic options that are likely to be more effective. Though minimally invasive procedures and personalized treatment options provide better patient care, imparting greater levels of information on even smaller tissue samples is challenging and places a greater burden on pathologists and consequences for patients.

Ancillary tests to answer the pertinent questions are frequently conducted on cell blocks, pellets of cells formed from the FNA sample, if available. Currently, there is no accepted laboratory standard on the preparation of cell blocks, though labs frequently employ one of several "homebrew" methods. When samples are large, cell blocks are easier to form, but with smaller samples, the "homebrew" methods may fail or result in a suboptimal cell block. Thus, there is a growing need to develop a standardized apparatus and method for preparing cell blocks in a low cost and efficient manner to provide answers to clinicians that impact therapeutic decisions.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described herein, one aspect of the disclosed subject matter includes a medical, e.g., cell block, apparatus. Such a cell block apparatus is useful for collecting and condensing a biological sample (e.g., cellular tissue, blood and/or mucus) into a cohesive pellet and separating it from any serum and fixative or solution added to preserve the cells for analysis. In some embodiments the medical apparatus comprises at least one elongate tubular body having a proximal end and a distal end defining an interior space therebetween, and a filter membrane disposed in the interior space between the proximal end and a distal end of the elongate tubular body. The filter membrane can be removable and sectionable (e.g., sliced into a plurality of pieces). The filter membrane can be disposed at a distal end of the at least one elongate tubular body or at a midpoint between the proximal and distal ends of the at least one elongate tubular body. In some embodiments, a filter assembly (which can likewise be removable and sectionable) can be provided which includes a base member coupled with the filter membrane, and the filter assembly being detachably coupled to the elongate tubular body. Additionally, the filter membrane (or assembly, if present) can include at least one alignment feature and/or at least structural reinforcement feature. In some instances, the filter membrane can include a plurality of peaks and valleys extending around at least a portion of its circumference. Further, some embodiments can provide a second elongate tubular body which telescopingly receives at least a portion of the first elongate tubular body. Additionally or alternatively, the second elongate tubular body can be removably attached to the first elongate tubular body. Furthermore, some embodiments can employ a cover for compressively engaging the filter membrane. Additionally, the apparatus can be disposable, or designed for repeated use and cleansing.

In an alternative embodiment, the medical apparatus comprises a first elongate tubular body having a proximal end and a distal end defining an interior space therebetween and a second elongate tubular body having a proximal end and a distal end defining an interior space therebetween. A filter membrane can be disposed in the interior space, and the first elongate tubular body can be at least partially disposed within the second elongate tubular body. The filter membrane can be disposed at the distal end of the first elongate tubular body, at a midpoint, or any alternative location between the proximal and distal ends of the first elongate tubular body. In some embodiments the first elongate tubular body includes at least one inwardly protruding support member (e.g., shelf, flange, etc.). Also, the filter membrane can include at least one structural reinforcement feature (e.g., lip, protrusion, etc.), the at least one structural reinforcement feature configured to engage the shelf of the first elongate tubular body.

In another embodiment, the medical apparatus comprises an elongate tubular body having a proximal end and a distal end defining an interior space therebetween with at least one support member disposed within the elongate tubular member, and a filter membrane disposed at a midpoint between the proximal and distal ends of the elongate tubular body with the filter membrane configured to engage the at least one support member. The at least one support member can be configured with a slot disposed therein which extends a distance less than the length of the at least one support member. Additionally, the at least one support member can include a flange which forms a sealing engagement with the interior of the elongate tubular member. In some embodiments, a second support member can be included, with the first support member disposed below the filter membrane and the second support member disposed above the filter membrane.

In another aspect of the disclosed subject matter, a method for preparing a collection of cells comprises positioning a filter membrane within an elongate tubular body, introducing a biological sample into the filter membrane, the biological sample including tissue (or solid particles) and fluid, and placing the elongate tubular body into a centrifuge. The assembly can then be centrifuged to separate the cellular tissue (or solid particles) from the fluid, with the tissue being retained on the filter membrane. The filter membrane can then be removed from the elongate tubular body, and sectioned into a plurality of pieces. In some embodiments the introducing a biological sample step is performed via fine needle aspiration. Additionally, positioning the filter membrane can include disposing the filter membrane within a base member, and/or compressing the tissue collected on the filter membrane with a cover. Additionally, the fluid retained within the elongate tubular body can be enclosed (e.g. with a cap) for parallel processing with the tissue collected from the filter membrane.

In another aspect of the disclosed subject matter, a medical kit is disclosed which comprises a needle, a first elongate tubular body having a proximal end and a distal end defining an interior space therebetween, the first elongate tubular body having at least support member one disposed therein, the first elongate tubular body configured for insertion within a second elongate tubular body, and a filter membrane. The filter membrane can be disposed in mating engagement with the at least one support member of the first elongate tubular body, and at a midpoint between the proximal and distal ends of the second elongate tubular body. Additionally, the filter membrane can be sectionable and/or disposable. Also, at least one of the first and second elongate tubular bodies can be reusable. Further, the filter membrane (and assembly, if present) can be provided separately, and/or in greater number than the remainder of the kit.

In another aspect of the subject matter a method is provided for preparing a cell block. The method includes introducing a biological sample into the elongate tubular body of the cell block apparatus. The cell block apparatus is then placed into a centrifuge for centrifuging to form a cellular pellet by separating the cells of the biological sample from the liquids, such as serum, and/or preservative/fixative. The use of the cell block apparatus for collecting the biological sample, as for example, from a needle, and centrifuging in the same container to form the pellet, helps reduce the cell loss from the biological sample that may occur if the sample were transferred from the original apparatus to an additional one for centrifuging.

In accordance with another aspect, a kit is provided. The kit includes a needle, e.g., for fine needle aspiration or biopsy, and a cell block apparatus. In some embodiments, the kit further includes a second filter assembly. The filter assemblies and/or the elongate tubular member may be disposable. In some embodiments, the filter assemblies are disposable and the elongate tubular members are reusable. In other embodiments, the entire cell block apparatus is disposable.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

FIG. 14A is an exploded view of an alternative exemplary embodiment of the disclosed subject matter;

FIG. 14B is a schematic diagram showing the assembled embodiment of FIG. 14A;

DETAILED DESCRIPTION OF SUBJECT MATTER

Reference will now be made in detail to select embodiments of the disclosed subject matter, examples of which are illustrated in the accompanying drawing. The method and corresponding steps of the disclosed subject matter will be described in conjunction with the detailed description of the system.

In accordance with the various embodiments of the disclosed subject matter, as summarized above and as described in further detail below, there is provided an apparatus for collecting and separating a liquid component from a cellular, or solid particle component, of a biological sample. While an exemplary embodiment disclosed herein includes fine needle aspiration, the apparatus and method of the disclosed subject matter is not limited to this exemplary embodiment and will be understood by an artisan of ordinary skill to be operable for collection and separation of any bodily fluids or specimens. In an exemplary embodiment, a disposable cell block apparatus and a method for using the apparatus, e.g., for tumor diagnosis, benign diagnosis, and other ancillary tests including research and development analyses, is provided. As used herein, the term "cell block" refers to a concentration of cells or solid particles from a biological sample, which is embedded in a medium, such as but not limited to paraffin wax. Thin sections from the medium with embedded cells are sliced or sectioned from the filter membrane of the cell block for mounting on a glass slide for analysis on a microscope or sliced from the cell block for other analyses. For example, visualization of the cells and the extracellular environment can provide information to determine whether the tissue collected is benign or malignant. Alternatively, the slices provide cellular material (DNA, RNA, proteins) for microcellular analysis. Although particular embodiments disclosed herein may focus on collection of the tissue or solid particle component in a biological sample for further diagnostics/testing, it will be understood by one of ordinary skill in the art that the disclosed apparatus and method is equally applicable for applications in which the fluid component of the biological sample is to be the subject of further diagnostics/testing.

Figure 1:
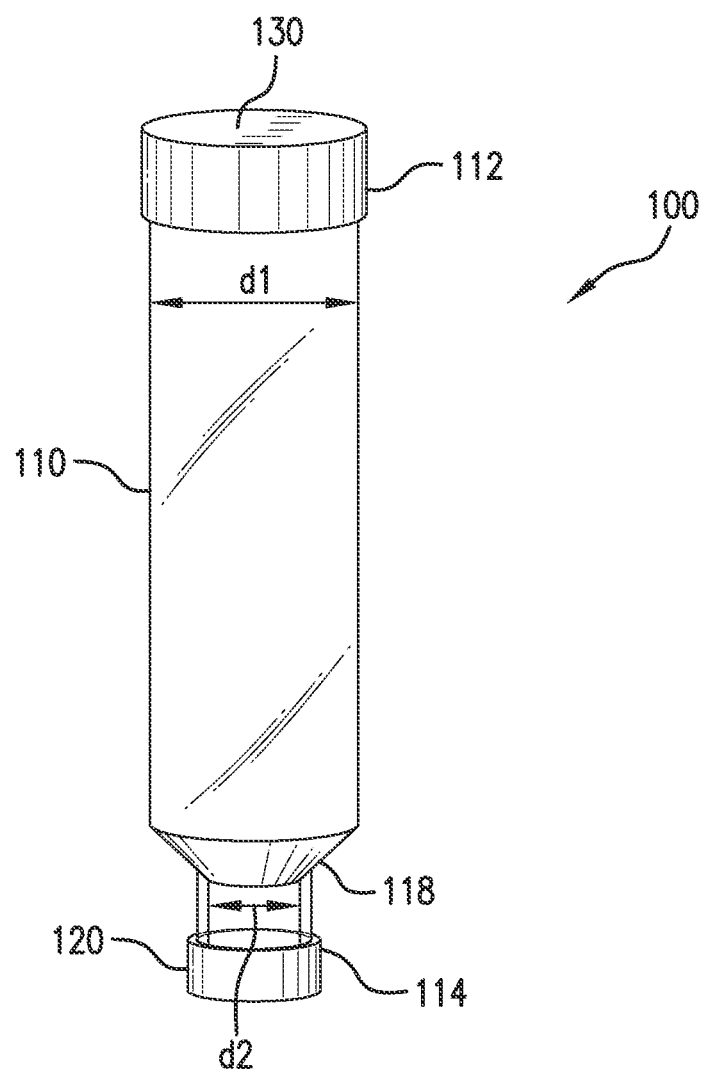
FIG. 1 is a schematic diagram showing an exemplary embodiment of the disclosed subject matter.

In one exemplary embodiment, the apparatus is configured as a cell block apparatus 100 is shown schematically in FIG. 1. Cell block apparatus 100 includes an elongate tubular body 110 and a filter assembly 120. The elongate tubular body 110 has a proximal end 112 and a distal end 114. In some embodiments, the elongate tubular body 110 has a first diameter ($d_1$) at the proximal end and a second diameter ($d_2$) at the distal end, wherein the second diameter is smaller than the first diameter. A section 118 disposed between the proximal end 112 and the distal end 114 of the elongate tubular body 110, has a decreasing diameter along a length thereof to define a generally conical distal section of the elongate tubular member 110. In some embodiments, a less gradual taper can be provided such that the elongate tubular body includes a step or abrupt restriction in diameter at 118. Various suitable volumes are available for elongate tubular body 110. For purpose of illustration and not limitation, suitable volumes include between about 15 ml to about 50 ml, or any other size that fits into a centrifuge, standard or otherwise. However, it will be understood by one of ordinary skill in the art that alternative sizes are within the scope of the disclosed subject matter. The elongate tubular body is sized to fit within a conventional centrifuge. In this manner, the cell block apparatus can receive the biological sample, for example, from a needle housing the biological sample obtained by fine needle aspiration techniques, and be disposed in the centrifuge for separation of the cells in the biological sample from any liquid to isolate and consolidate the cells into a concentrated pellet by centrifugation. Using the same unit for receiving the biological sample and separating the biological sample into component parts reduces the loss of sample size and reduces risk of contamination due to exchange between multiple components. In some embodiments, the elongate tubular body is suitable for relative centrifugal forces of between about 1,200 to about 16,000 RCF. For example, 12,000 RCF, 1,200 RCF, 16,000 RCF, 2,000 RCF, 9,400 RCF, 7,500 RCF. For further illustration in one embodiment, the elongate tubular member has a volume of 15 ml, and is suitable for centrifugation at 1,200 RCF or 12,000 RCF. In other embodiments, for example, the elongate tubular member has a volume of 50 ml and is suitable for centrifugation at 16,000 RCF or 2,000 RCF or 9,400 RCF. The elongate tubular body of the device can be formed of various materials and in particular various polymers, for example, polypropylene and/or polystyrene. Further, the materials used for the elongate tubular body, filter assembly, or compressive cover, which is described below, can be biodegradable materials.

Figure 2:
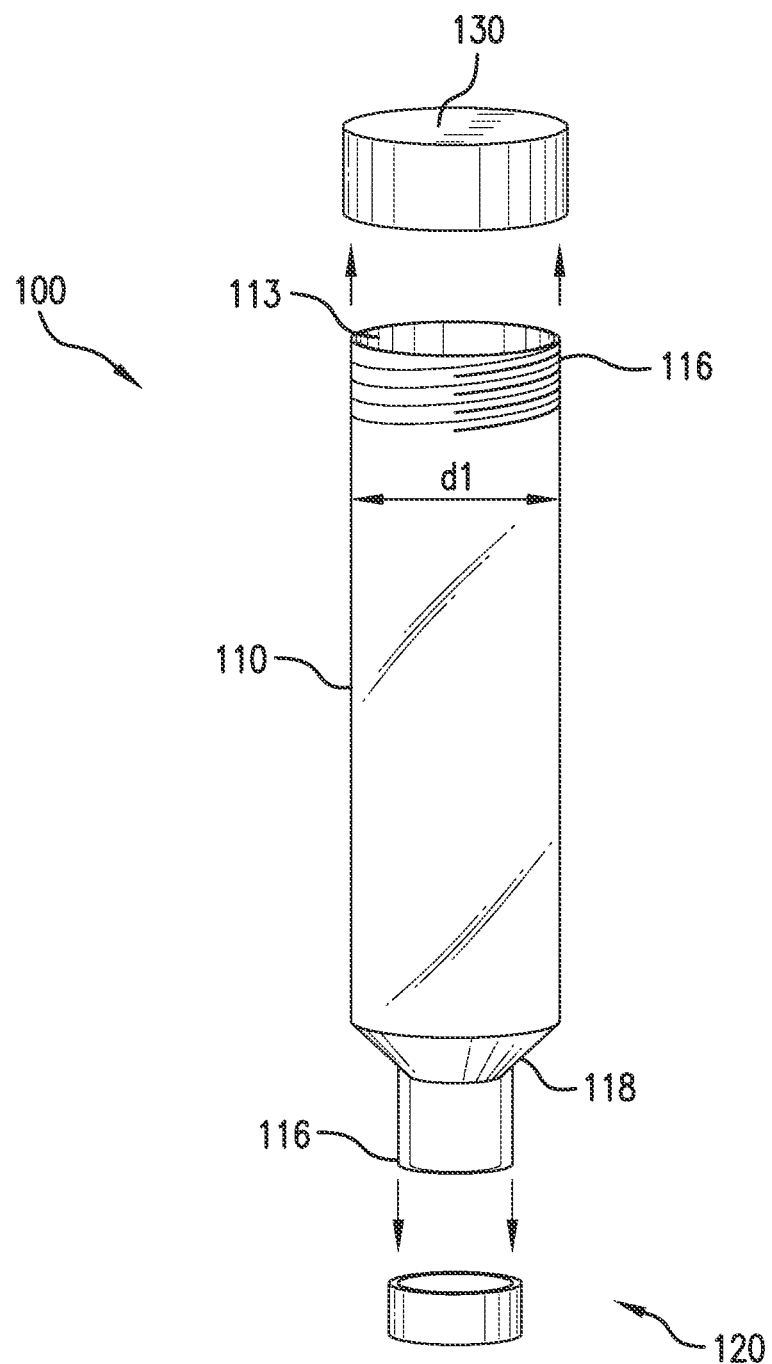
FIG. 2 is a schematic diagram showing an exploded view of the disclosed subject matter of FIG. 1.

Referring to FIG. 2, the elongate tubular body 110 defines an opening 113 at the proximal end of the body. In some embodiments, the opening 113 is closed by a lid 130. The lid can be configured with thread (not shown) to engage threads 116 disposed on a proximal section of the elongate tubular body 110. However, other suitable methods and features can be used to engage the lid 130 and elongate tubular body 110, such as interference fit or other methods of engagement, as would be appreciated by one of ordinary skill in the art. In one embodiment, the lid can be a stopper formed from a self sealing or resealable material. In this regard, the lid 130 is puncturable by a needle allowing transfer of the biological sample from the needle to the interior of the elongate tubular body. After deposit of the biological sample and removal of the needle from the lid 130, the material self-seals the puncture created by the needle entry. In the exemplary embodiment illustrated in FIG. 2, at the distal most end 116 of the elongate tubular body 110 the structure is configured to permit the filter assembly 120 to engage. In one embodiment, the material of the neck 116 has a thickened wall to allow the filter assembly 120 to securely engage the elongate tubular member 110. Further, the outer surface of the neck 116 can be configured with a thread or a plurality of threads to permit the base member 124 to securely engage the elongate tubular body 110.

In some embodiments, the elongate tubular body is preloaded with a fixative. A "fixative" as used herein refers to a compound, such as formalin, ethanol, methanol, RPMI, saline for preservation of the cells.

Figure 3:
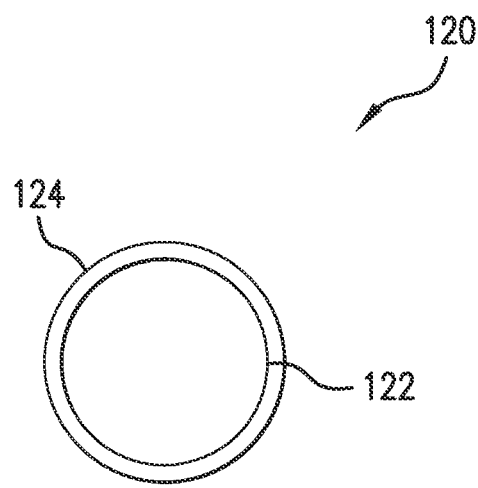
FIG. 3 is a schematic diagram of the filter assembly from a top view perspective, including a filter membrane and a base member.
Figure 4:
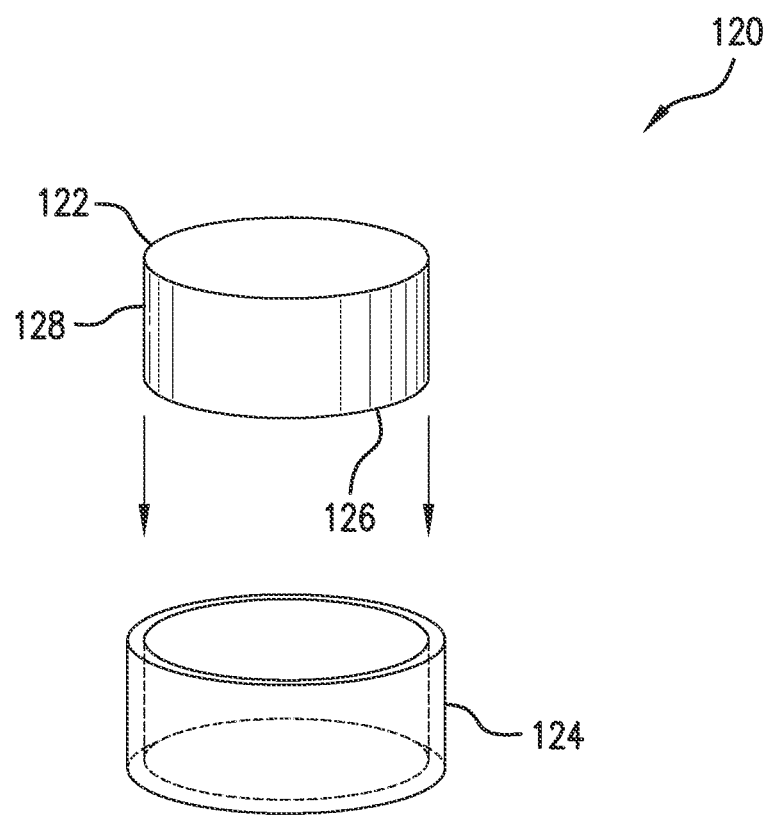
FIG. 4 is a schematic diagram of one embodiment of the filter assembly of the disclosed subject matter.

Referring to FIG. 3, a top view of a filter assembly 120 in accordance with the subject matter is provided. In an exemplary embodiment, the filter assembly 120 comprises a base member 124, such as a non-porous member, and a filter membrane 122 that is disposed within the body of the base member. Thus, in one embodiment, the filter assembly is removable. Additionally, the entire filter assembly, including filter membrane 122 is sectionable, i.e., capable of being cut or sliced into pieces or "sections" e.g., for mounting on a glass slide for analysis on a microscope or for other analyses such as microcellular analysis, e.g., DNA, RNA, and/or protein. As illustrated in FIG. 4, the filter membrane 122 is sized sufficiently smaller than the base member 124 so that it can slide into the interior space defined by the base member 124. In some embodiments, the filter membrane includes sidewalls formed of paraffin, paraform, plastic, rubber or foam. Referring back to the exemplary embodiment depicted in FIG. 1, the filter assembly 120 is associated, or coupled, with the distal end of the elongate tubular member. In this respect, the base member 124 can be configured with threads or some other engaging member to engage a distal portion of the elongate tubular body 110, and the filter membrane 122 member can be sized to engage the distal end of the elongate tubular member, for example, by an interference fit. The engagement of the filter membrane with the interior surface of the elongate tubular body provides a seal to prevent leakage around the periphery of the filter membrane. Consequently, any fluid within the distal portion of the elongate tubular body must first pass through, and be filtered, by the filter membrane. Thus, in this exemplary embodiment, the filter membrane 122 can be slidably received by the distal portion (e.g., neck) of the elongate member. The filter assembly 120 is detachable from the elongate tubular body. As described in detail below, the detached filter assembly 120 and its contents can be enclosed by a compressive cover 200 (as shown in FIG. 8).

The filter membrane 122 has a porosity sufficient to maintain the cells or cellular components from the biological sample while the liquid and fixative pass through. In some embodiments, the liquid is the fixative. However, in other embodiments, the liquid and fixative may be a mixture. For purpose of illustration and not limitation, in some embodiments the filter membrane 122 has pores between about 0.4 µm to about 5 µm. The pore density can be about $1\times10^8$ to about $6\times10^5$ pores/cm$^2$. Thus, in some embodiments, the filter membrane has a porosity of 5.0 µm and a pore density of $6\times10^5$ pores/cm$^2$. In other embodiments, the filter membrane has a porosity of 5.0 µm and a pore density of $1\times10^8$. However, suitable porosity and pore density can be selected depending on the cells targeted for capture. In some embodiments, the filter membrane has a thickness of about 9 to about 100 µm, such as 17 µm. Although specific ranges are provided for exemplary purposes, it will be understood by one of ordinary skill in the art that alternative sizes are within the scope of the disclosed subject matter. Suitable materials can be used to from the filer membrane. For example, in one embodiment the filter membrane is formed from polyethylene terephthalate.

Figure 5:
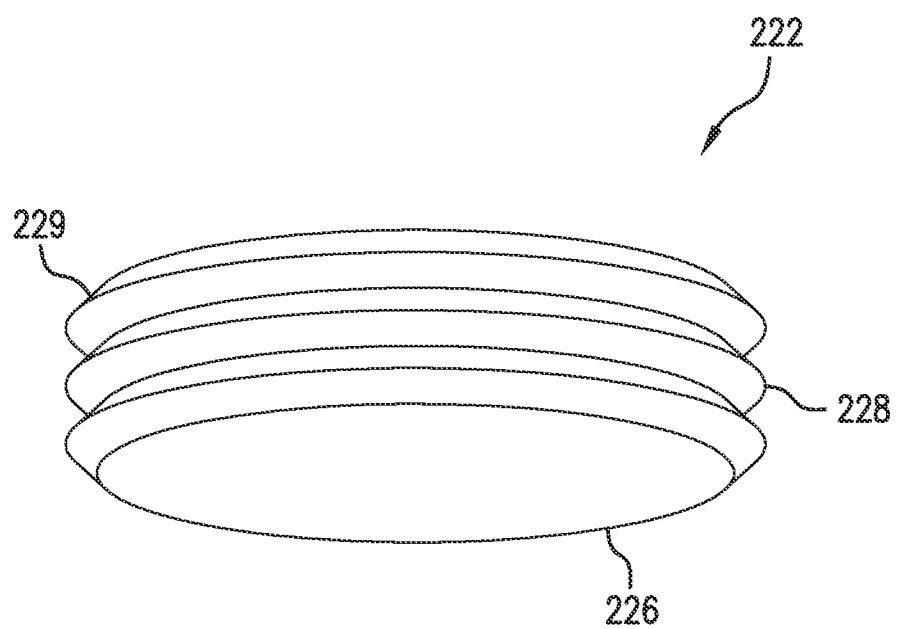
FIG. 5 is a schematic diagram of another exemplary embodiment of the filter membrane of the disclosed subject matter.
Figure 7:
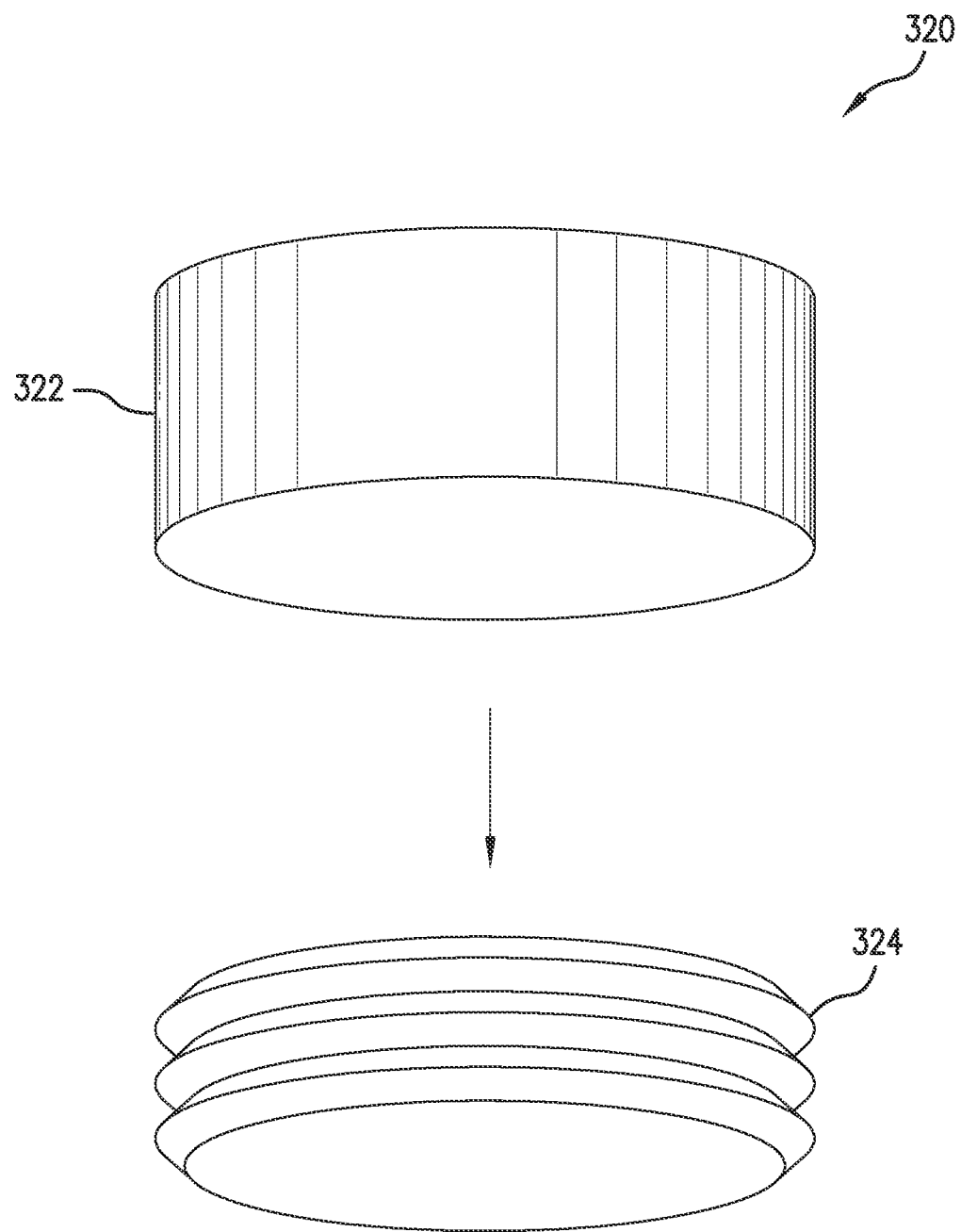
FIG. 7 is a schematic diagram of another exemplary embodiment of the filter assembly of the disclosed subject matter, including a filter membrane and a bellowed base member.

The filter membrane 122, as illustrated in FIG. 4, has a planar bottom surface 126 and an upwardly extending wall 128 around the periphery of the planar bottom surface 126. The upwardly extending wall can, in some embodiments, have a planar surface. Alternatively, as schematically shown in FIG. 5, the filter membrane 222 can include an upwardly extending wall 228 having one or a plurality of bellows 229 or a plurality of threads. In an alternative embodiment, as illustrated schematically in FIG. 7, the filter assembly 320 can include base member 324 having an upwardly extending wall with bellows and a filter membrane 322 having a planar side wall. In some embodiments, the bellows provide the capability of the base member or the filter membrane to adjust to sample size. The bellowed side wall compresses the cells into a tablet, which further facilitates an even distribution of cells. For example, in some instances, the smaller the sample, the greater the bellows will expand to create a compact pellet. The filter membrane and the base member permit essential fluids for fixation and processing to enter the base member but do not allow the cells to pass through. Thus, the cells remain on the filter membrane.

While the filter assembly in the exemplary embodiments is depicted as two discrete members (i.e. a filter membrane and base member), alternative configurations (e.g., an integrally formed and unitary filter assembly) will be understood by artisans of ordinary skill to be within the scope of the disclosed subject matter.

The combination of cells can be embedded in paraffin and cut, within the filter assembly or separately, into slices for diagnosis and ancillary tests. In other words, the filter membrane's structural characteristics allow for a blade to slice through the membrane and base member without flaking or splintering such that no unwanted debris is produced that might contaminate or compromise the pellet retained within or on the membrane. Further, the filter assembly is of sufficient rigidity to maintain its form and orientation indicia (described in further detail below), yet is sufficiently malleable and flexible so as to avoid damaging the cutting blade.

In this manner, the presently disclosed subject matter provides for a method for preparing a cell block in which the filter assembly remains with the specimen throughout processing to eliminate the risk of particle loss and cross contamination that can occur during various procedural steps, which involved eight transfers under prior art techniques. Additionally, the disclosed subject matter provides a standardized technique for processing samples which allows for more consistency and accuracy to pathological evaluations. In some embodiments, the method comprises introducing a biological sample into a cell block apparatus described herein. The cell block apparatus containing the biological sample is disposed into a centrifuge to centrifuge the biological sample for a sufficient amount of time to separate the cells, or tissue, from the liquid component and form a pellet. Again, for purpose of illustration and not limitation, the biological sample can be centrifuged at relative centrifugal forces of between about 1,200 to about 16,000 RCF for about five to ten minutes, or longer as necessitated by the nature and amount of biological sample collected. Although specific ranges are provided for exemplary purposes, it will be understood by one of ordinary skill in the art that alternative centrifuge times are within the scope of the disclosed subject matter.

The pellet is then processed, for example, in a cassette though any alternative suitable housing can be employed. The cassette is placed in formalin and into a tissue processor for processing through several steps (including dehydration to remove any aqueous solutions, then clearing of dehydrant, and finally infiltration by an embedding agent, such as paraffin). The processing time of the cellular pellet varies upon the tissue processors. In one embodiment, the processing time is less than about three hours. Then the processed pellet is embedded into a medium to form a cell block. The medium, can be for example, paraffin, paraform, or the like. Various materials can be used for the embedding step.

In accordance with another aspect of the disclosed subject matter, multiple cell blocks can be formed simultaneously via batch processing in under about three hours. In such batch processing applications, a plurality of cell block apparatuses (each including an elongate tubular body having an interior space) is associated with a respective detachable filter assembly disposed in communication with the interior space of the elongate tubular body. As described above, in some embodiments the filter assembly includes a base member configured to engage the distal end of the elongate tubular body, and a membrane having a porosity of between about 0.4 µm to about 10.0 µm. Although an exemplary range is provided for illustrative purposes, it will be understood by one of ordinary skill in the art that alternative sizes are within the scope of the disclosed subject matter. Multiple biological samples, same or different, can be introduced into the cell block apparatuses. The elongate tubular bodies can be interconnected or configured as discrete units. The elongate tubular bodies are each sized sufficiently to fit into a centrifuge device configured with a plurality of receptacles to receive the plurality of elongate tubular bodies of the cell block apparatuses. Upon completion of the centrifuge cycle, the biological samples in each cell block apparatus forms a cellular pellet ready for individual processing or embedding into a plurality of cell blocks. Accordingly, the method disclosed herein can achieve an array of cell blocks.

Figure 6:
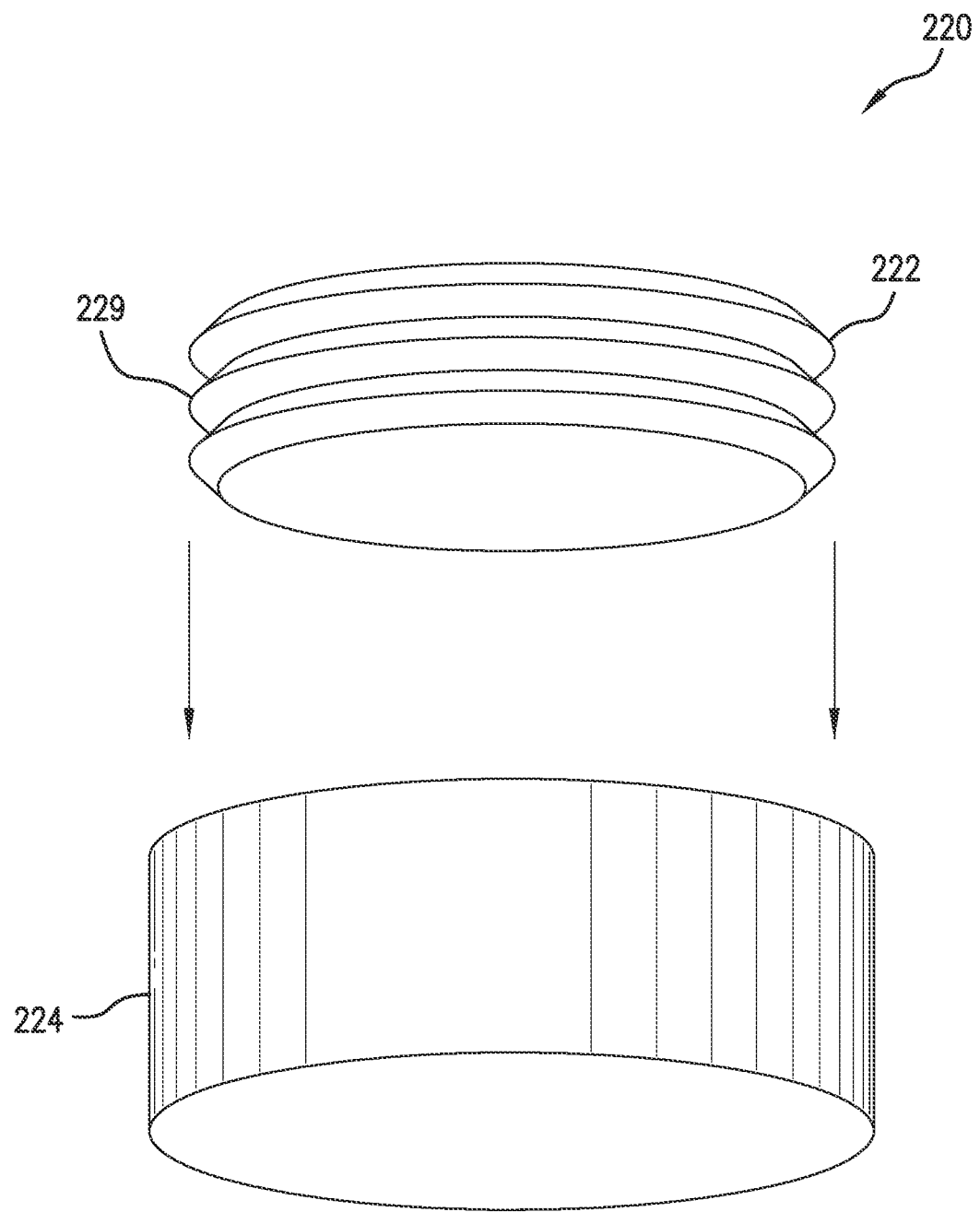
FIG. 6 is a schematic diagram of an exemplary embodiment of the filter assembly of the disclosed subject matter, including a bellowed filter membrane of FIG. 5 and base member.

In accordance with another aspect of the subject matter, the apparatus and system disclosed herein can be configured as a kit, or collection of discrete components designed to function as a unit. The kit includes a needle, such as but not limited to a fine aspiration needle, and a cell block apparatus described above. In some embodiments, the elongate tubular member is preloaded with a fixative. The kit may include a second, replaceable, filter assembly. Referring to FIG. 6, the second filter assembly 220 may include a base member 224 and a filter membrane 222 having a planar bottom surface and wall upwardly extending from the planar bottom surface of the filter membrane. The upwardly extending wall can include one or a plurality of bellows 229 or plurality of threads. In another embodiment, a kit is provided which provides one or more filter assemblies for samples that are not associated with a large quantity of liquid or blood. Tissue sealed in the filter assembly can then be placed in a container of formalin for clinicians performing FNAs or biopsies. In such instances, for example, the specimen does not need to be centrifuged in a tubular structure. Instead, it can be embedded in the filter assembly and undergo histology directly.

Figures 8A, 8B:
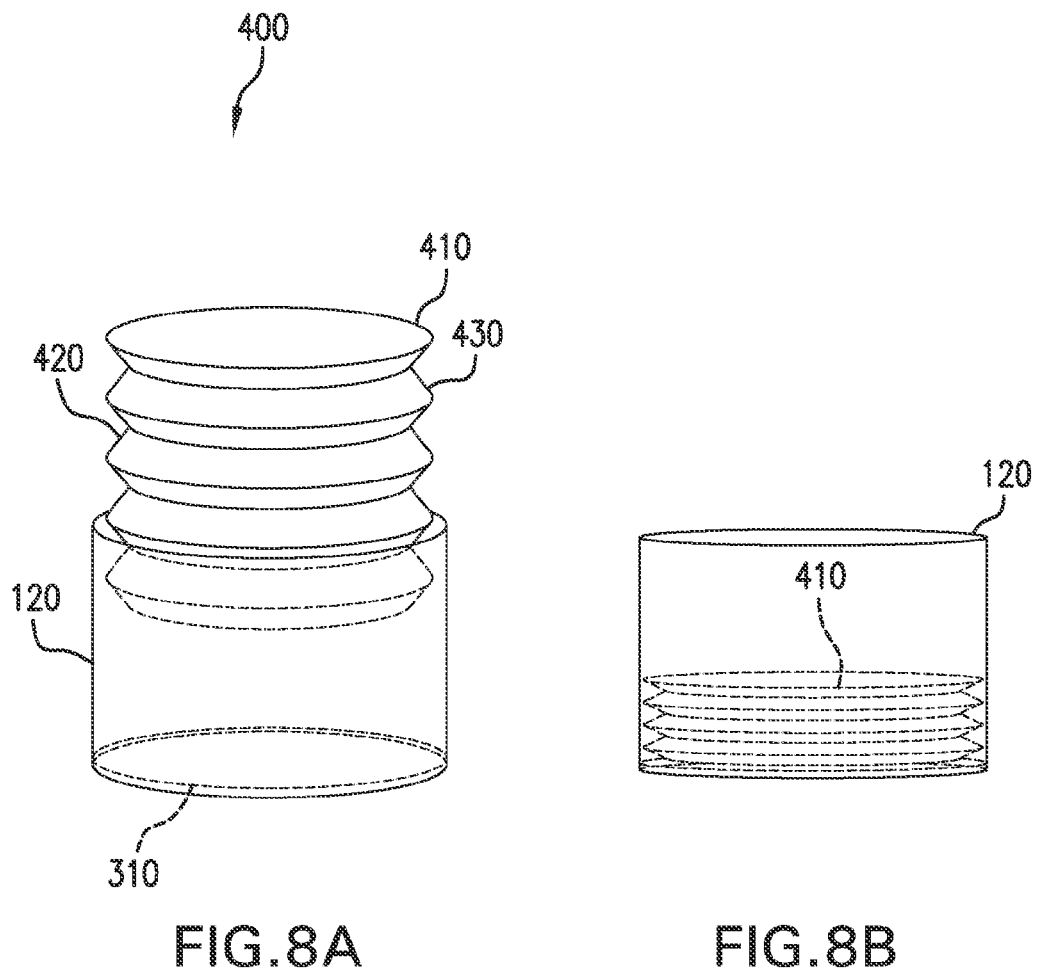
FIGS. 8A-D are schematic diagrams showing perspective views of a filter assembly and a compressive cover in accordance with the disclosed subject matter.
Figure 8C:
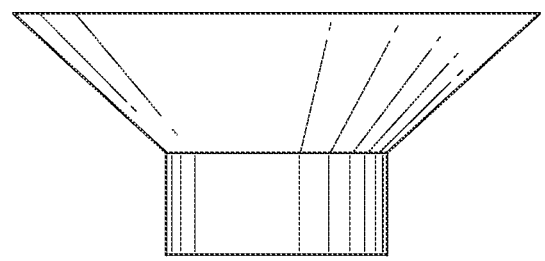
Figure 8D:

In yet another embodiment, as illustrated in FIGS. 8A and 8B, a filter assembly 120 is provided (as described above), which includes a compressive cover 400. As illustrated in FIG. 8A the filter assembly 120 can include a tissue sample 310. The compressive cover 400 is disposed within the filter assembly 120 and is able to close the filter assembly so that the contents are enclosed in a sealed manner. In this regard, the compressive cover can be configured with a planar top surface 410 that serves as a cap. The compressive cover 400 includes a planar bottom surface and a sidewall 412. As illustrated, the sidewall 412 can include a plurality of bellows 430, which can contract and expand. When in a contracted state (shown in FIG. 8B), a compressive force is exerted on the sample 310 contained within the filter assembly 120. Additionally or alternatively to the structural features described above which facilitate the generation of compressive forces, the cover can be formed of elastomeric material with innate compressive and expansive properties to enhance the compressive force exerted on the collected sample and filter membrane. The application of pressure to the sample 310 concentrates and constrains the sample. Additionally, the compressive cover facilitates an even distribution of cells and also helps the paraffin to penetrate the sample 310 to provide improved embedding of the cells of the tissue sample. Further, the compressive cover 400 serves to close the filter assembly from the external environment, thereby preserving the integrity of the collected tissue sample.

The compressive cover can have a planar surface formed from the same filter membrane material as that on the filter assembly. For example, in one embodiment, the compressive cover is lined by a filter membrane, which can be similar in pore size, thickness and density as the filter membrane 122 of the filter assembly 120. In another example, the compressive cover has a planar surface having a porosity of between about 0.4 µm to about 10.0 µm. Although an exemplary range is provided for illustrative purposes, it will be understood by one of ordinary skill in the art that alternative sizes are within the scope of the disclosed subject matter. The use of a compressive cover is advantageous in that it eliminates the need for more complex equipment and processes (e.g., hydraulic, vacuum and pneumatic regulators) to condense the tissue, remove excess liquid, and contain all cells.

Although FIGS. 8A-B depict generally circular compressive covers, alternative geometries such as a bowl shape (FIG. 8C) or elliptical-disc shape (FIG. 8D) can be employed if so desired. Similarly, alternative embodiments can include covers with non-planar bottom or top surfaces such that the cover can impart a pattern or non-uniform distribution of the collected sample, as well as covers having different diameters than the filter membrane. Also, the covers can include a retention mechanism (e.g., latch, tongue-groove coupling, etc.) for engagement with a corresponding structure on the filter assembly to lock or retain the sample on the filter membrane. Such an enclosure is advantageous in preventing debris from contaminating the collected sample, as well as facilitating storage and/or transport of the collected sample, if so desired.

The filter assembly 120 and compressive cover 400 together, for example, can be used for non-FNA specimens, such as biopsies. For example, the specimen can be placed directly in the filter assembly at the time the clinician removes the tissue from the patient (rather than placing loose piece(s) of tissue in jar of formalin to be handled by pathology laboratory personnel thereafter). Such application is advantageous in that it: (1) eliminates the chance of cross contamination which is possible with transferring and handling tissue multiple times; (2) eliminates the loss of minute pieces of tissue with multiple transfers; and (3) prevents leaving a specimen behind in a formalin jar, for example, because the specimen was inadvertently undetected. Typically, tissue samples are transferred from different media and/or containers several times before being ready for cutting for microscopic examination. The filter assembly and compressive cover disclosed herein serve to overcome the disadvantages of such procedures.

Figures 9A, 9B:
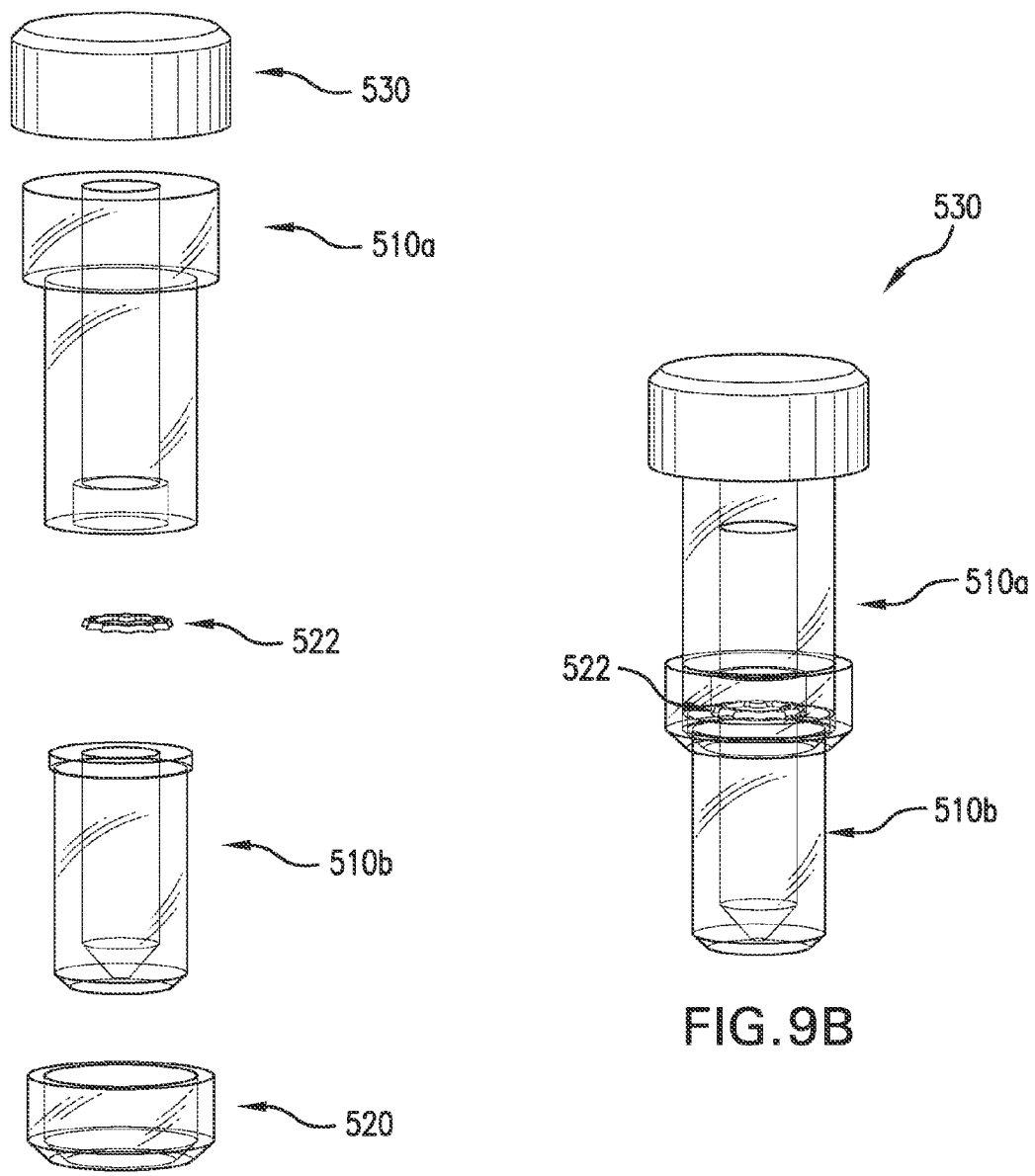
FIG. 9A is an exploded view of an alternative exemplary embodiment of the disclosed subject matter.
FIG. 9B is a schematic diagrams showing the assembled embodiment of FIG. 9A.

In another exemplary embodiment, the elongate tubular body can be configured of multiple pieces 510a, 510b with a filter membrane 522 can be disposed between pieces 510a and 510b, e.g., at the midpoint of the assembled tubular body, as depicted in FIGS. 9A-B. It is to be understood that although specific reference may be made only to the filter membrane in the exemplary embodiments disclosed below, it is within the scope of the disclosed subject matter to include a cover and base member with the filter membrane, if so desired. In this exemplary embodiment of FIGS. 9A-B, the filter membrane 522 is clamped between the two tubular portions 510a and 510b to capture particulates while liquid passes from 510a to 510b during centrifuging. The lower tubular member 510*b* can be configured with a lip or recess proximate on its upper end to receive the filter membrane 522 therein. Alternatively, the upper tubular member 510*a* can be configured with a support member, such as shelf or flange (described in further detail below), which receives the filter membrane 522 therein. Locating the filter membrane at the midpoint of the tubular body is advantageous in that such a configuration results in the reservoir disposed above the filter membrane to be of equivalent size as the reservoir below the filter membrane, and therefore equivalent amounts of fluid can be contained within each reservoir. However, the filter membrane can be disposed at alternative locations closer to the top or bottom of either tubular portion 510*a*, 510*b* is within the scope of the disclosed subject matter.

The elongate tubular pieces 510*a*, 510*b* can be attached, e.g., by via a interference fit or a threaded engagement between the respective inner and outer sidewalls. Although the exemplary embodiment depicted in FIGS. 9A-B depict the upper tubular member 510*a* as the male component and the lower tubular member 510B as the female component, these configurations can be reversed, as so desired. Additionally, or alternatively, the tubular members can be formed with an equivalent inner and outer diameters, and coupled by any suitable device, e.g., magnets.

Figure 9C:
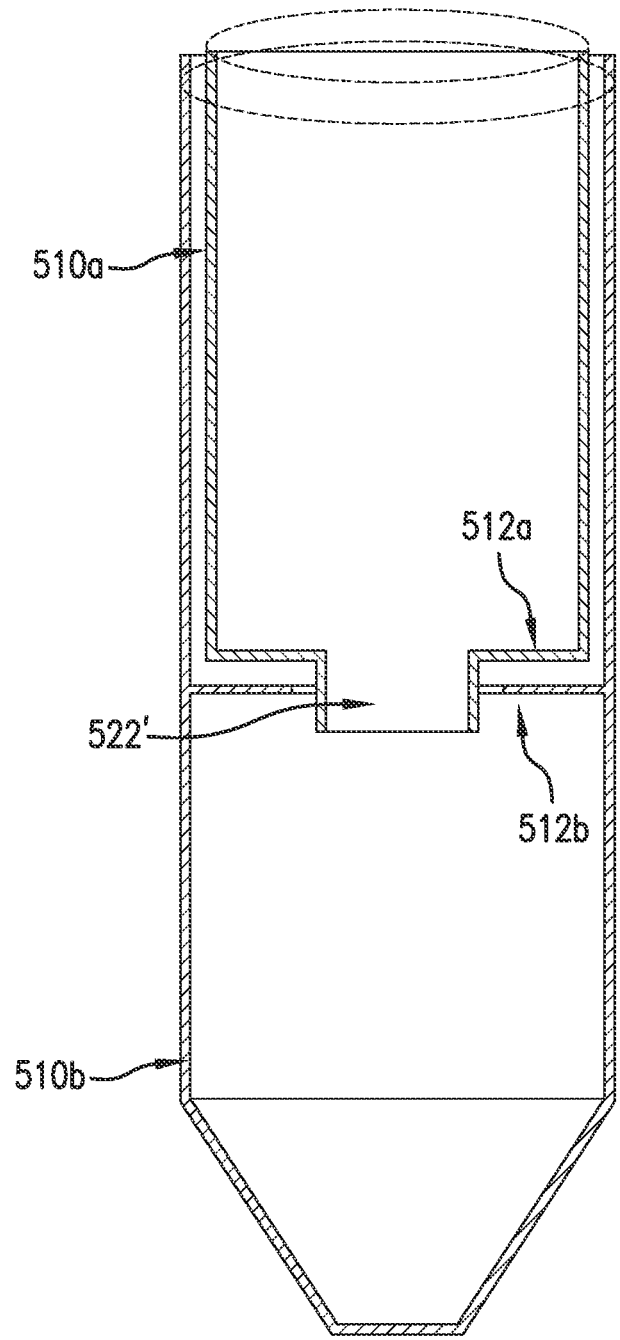
FIG. 9C is cross-sectional view of an alternative exemplary embodiment of the disclosed subject matter.

In another exemplary embodiment, the tube pieces 510*a*, 510*b* can be configured such that one of the pieces is received, at least partially, in a telescoping manner within the other as shown in FIG. 9C. In the embodiment illustrated in FIG. 9C, the upper tube 510*a* can have a bottom portion with a platform for the filter assembly that would fit at 522' and a circumscribing shelf or lip 512*a* configured to rest against an inwardly protruding lip or shelf 512*b* formed in the lower tube portion 510*b*. Additionally or alternatively, the inwardly protruding shelf 512*a* can also receive the filter membrane. Further, the dimensions of the protruding shelves 512*a*, 512*b* can vary both in terms of the cross-sectional thickness as well as the distance the lips radially protrude so as to accommodate filter membranes of varying sizes. The elongate tubular pieces 510*a*, 510*b* can be attached via an interference fit, a threaded engagement between the respective inner and outer sidewalls, or via mating engagement between shelves 512*a* and 512*b*.

Figure 9D:
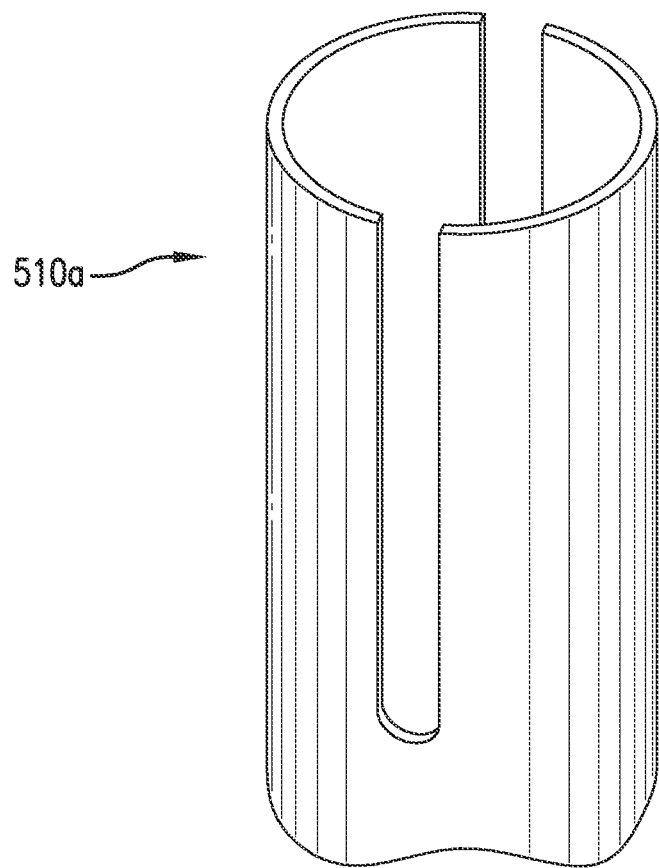
FIG. 9D is schematic diagram of a tubular member in accordance with the embodiment of FIG. 9C.

In some embodiments comprising two elongate tubular members, the inner tubular member 510*a* can be formed with a slot or channel formed in the sidewall which extends along the longitudinal axis of the tubular member, as shown in FIG. 9D. This slot is sized to receive the filter membrane and allows for rapid removal of the filter membrane after the centrifuge process, without the need to disassemble the two elongate tubular members. Although the exemplary embodiment of FIG. 9D depicts vertical slots, alternative designs (such as a staggered or tortious path) are within the scope of the disclosed subject matter. Such tortious path designs can be advantageous in requiring deliberate and careful removal of the filter membrane, thereby preventing accidental removal or dislodgment of the filter membrane after the centrifuging process.

Figure 10A:
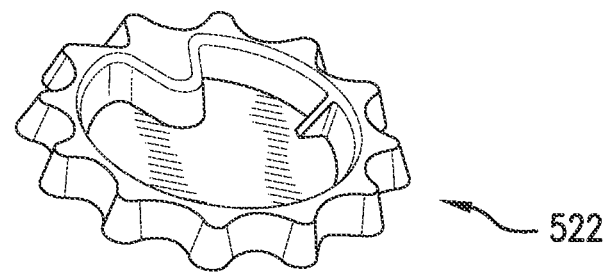
FIGS. 10A-H are schematic diagrams of another embodiment of the filter membrane of the disclosed subject matter.
Figure 10B:
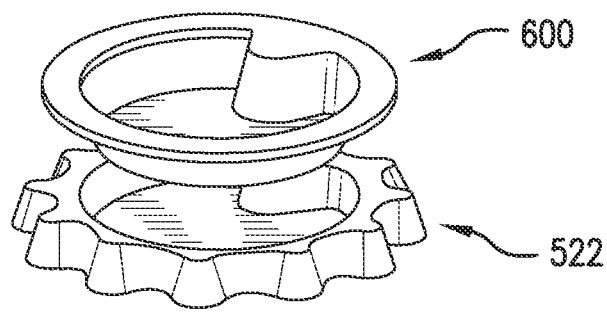
Figure 10C:
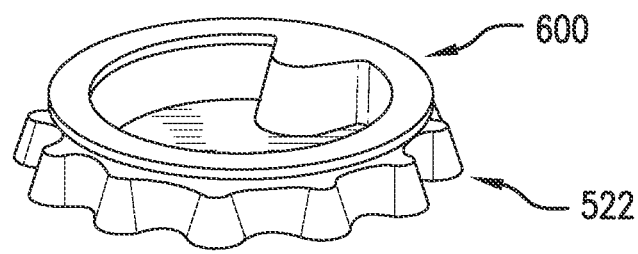
Figure 10D:
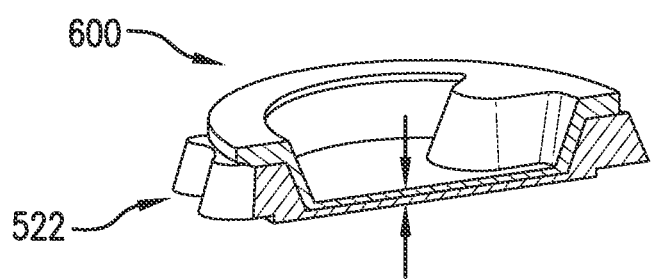

As previously described above with respect to FIGS. 8A-D, some embodiments of the disclosed subject matter can employ a compressive cover or cap to facilitate the concentration and isolation of the collected sample on the filter membrane. For example, the filter membrane 522 of FIG. 10A can be configured to receive a cover 600 which matingly engages the filter membrane 522 as shown in FIGS. 10B-D. As indicated by the arrows depicted in FIG. 10D, the cover 600 can apply a compressive force to concentrate and constrain the particulate for subsequent steps, such as dehydration, clearing, infiltration, etc. The compressive force exerted by the cover 600 can be supplied by the technician, or by an external device (not shown) such as a spring-loaded plunger.

Figure 11A:
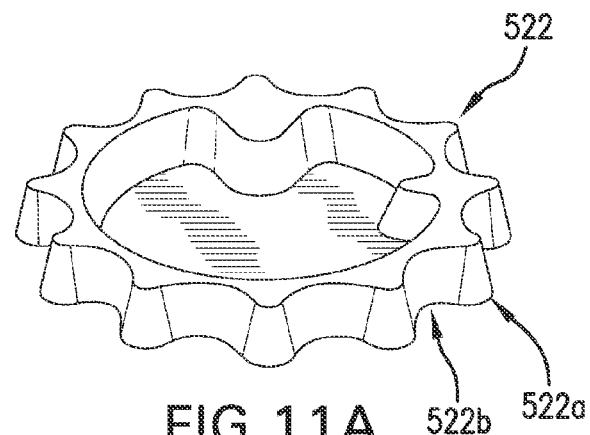
FIGS. 11A-C are schematic diagrams of another embodiment of the filter membrane of the disclosed subject matter.
Figure 11B:
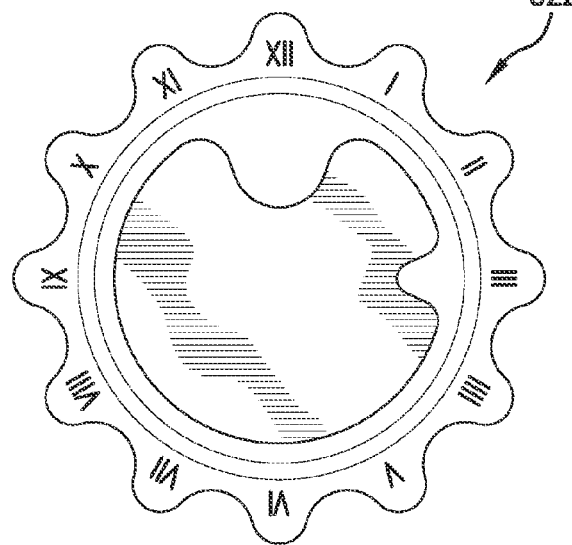
Figure 11C:
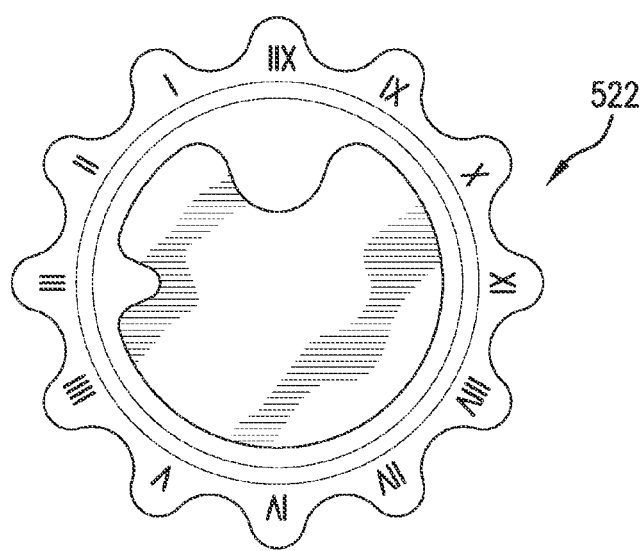
Figure 11D:
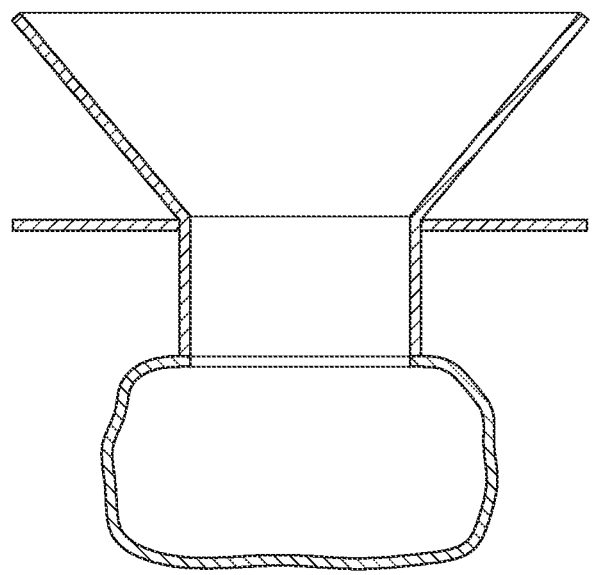
FIG. 11D is a cross-sectional view of another embodiment of the filter membrane of the disclosed subject matter.

In accordance with an aspect of the presently disclosed subject matter, the filter membrane 522 includes alignment features illustrated in the exemplary embodiment as roman numeral indicia, as shown in FIGS. 11B-C. This indicia allows users to easily and precisely reference a specific region of interest (e.g., location "III", or the "three-o'clock position"). Additionally, the indicia allow for different slices of the filter membrane to be oriented as so desired with respect to each other, as well as evidencing whether the filter membrane 522 is flipped or inverted. The filter membrane 522 can be formed with alternating peaks 522*a* and valleys 522*b* around its circumference, as shown in FIG. 11A, to increase the surface area and provide greater stability and reliability during both the centrifuge step as well as the subsequent sectioning (i.e. cutting). In addition to this indicia, the border of the filter membrane can be formed with a greater thickness than the porous filter portion, and serve as a gasket which forms a seal with the interior surface of the tubular body. Further, this border portion can be formed of opaque material which further serves as a visual aid to easily identify particular areas of interest in the sample collected on the inner porous material. Furthermore, this border portion of the filter membrane can be formed of a porous material, e.g. open cell foam or foam rubber, which allows the cutting blade to easily slice through the filter membrane without excessive force, thereby eliminating any undesired buckling of the filter membrane, damage to the blade, or splintering or flaking of the filter membrane. Additionally, the filter membrane can be formed separately from the remainder of the filter assembly (e.g., the porous filter membrane which serves to separate the tissue(s), or cell block, from the collected sample of fluid/tissue can be distinct from the surrounding frame having the undulating structure and indicia as shown in FIG. 10A). The porous filter membrane can be attached to the surrounding structure via adhesive or ultrasonic welding.

Figure 10F:
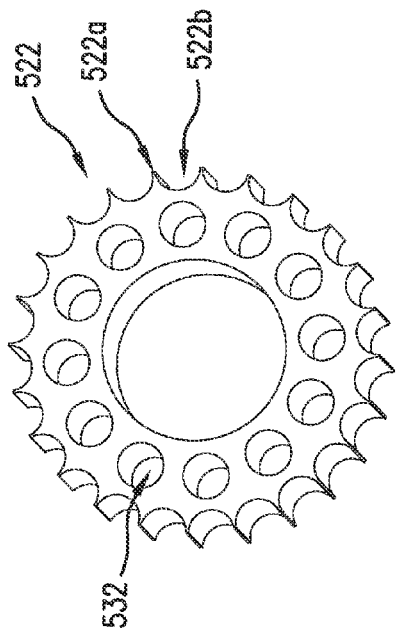
Figure 10H:
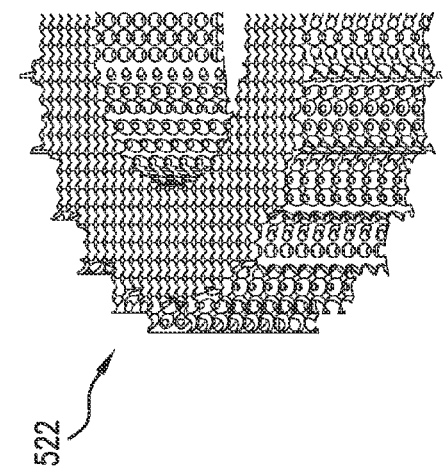
Figure 10E:
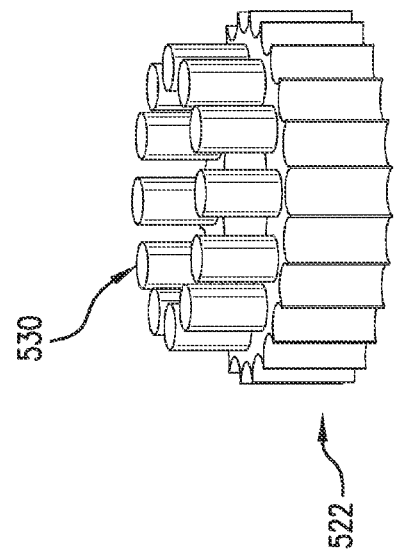
Figure 10G:
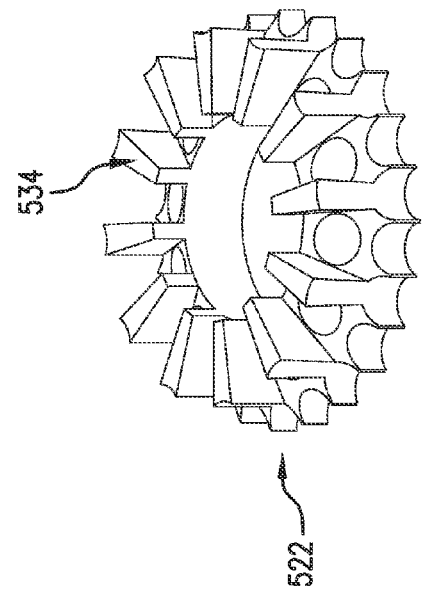

In further regards to the structure of the filter membrane (or assembly, if present), and as disclosed above, the increase in surface area provided by the peaks and valleys formed in the periphery of the filter membrane (or assembly, if present) facilitates integration with the embedding medium (e.g., wax) and improved anchoring of the filter membrane. The number of peaks and valleys can be varied as so desired, and in some embodiments the peaks and valleys are configured as obtuse rounded edges (FIGS. 10A-D), whereas in other embodiments the peaks and valleys are formed as acute apices (FIGS. 10E-F). Additionally or alternatively, the filter membrane 522 (or assembly, if present) can be formed recesses 532, as illustrated in FIGS. 10E-G, which similarly increase the surface area for engagement of the filter membrane with the embedding medium. In other embodiments the filter membrane can be formed with surface features, such as cylindrical posts 530 (FIG. 10E) or ribs 534 (FIG. 10G) which also increase the surface area for engagement with the embedding medium. Additionally or alternatively, as illustrated in FIG. 10H, the filter membrane can be formed as a porous member, e.g. foam, which permits the embedding medium to penetrate through and infiltrate the entire filter membrane and/or assembly. In each of these embodiments, the enhanced engagement and integration of the filter membrane with the wax results in a more reliable and consistent sectioning. Moreover, the various structural features described above (e.g. peaks/valleys, holes, ribs, porous foam) for increasing the surface area of the filter membrane also allow for a user to selectively orient the filter membrane during assembly, sectioning, and/or placing in a diagnostic apparatus (e.g. microscope).

Although the particular exemplary embodiments of the filter membrane shown in FIGS. 10-11C depict a generally circular filter membrane formed of a semi-rigid material, alternative configurations of filter membrane geometries and construction are within the scope of the disclosed subject matter. For example, the filter membrane can be configured as a flexible bag-like member, as shown in FIG. 11D. The bag-like filter membrane is made with a desired porosity, as described above, and provides an amorphous shape which allows the membrane to distort as needed under the forces generated during the centrifuge process, which can relieve some of the stresses that may be imparted on the other components of the apparatus when a rigid filter membrane is employed. Additionally, such a flexible bag-like filter embodiment allows for greater design flexibility in that the amorphous filter can accommodate differing volumes of cells. Furthermore, the amorphous bag-like structure effectively increases the surface area through which the biological sample passes, which in turn expedites the filtration process and minimizes the risk of clogging the filter membrane in applications of cellular specimens. The exemplary embodiment depicted in FIG. 11D illustrates a filter membrane which also includes structural reinforcement features, described in further detail below.

Figure 12A:
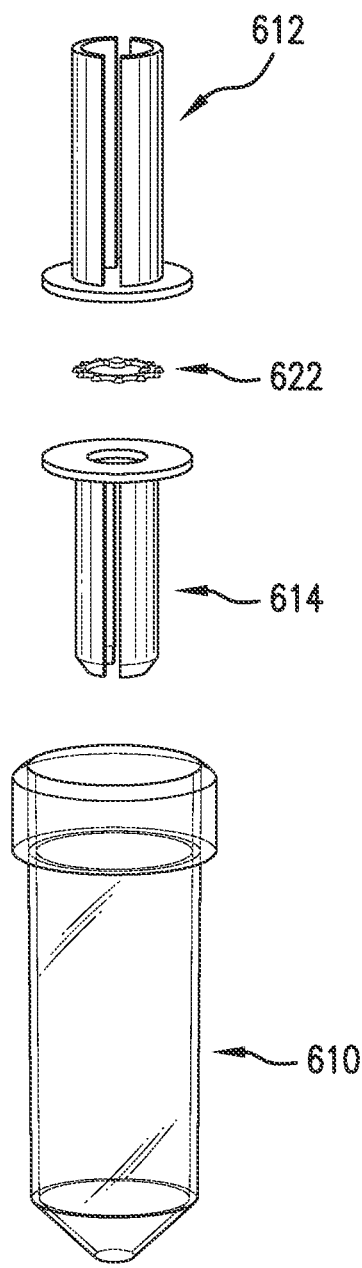
FIG. 12A is an exploded view of an alternative exemplary embodiment of the disclosed subject matter.
Figure 12B:
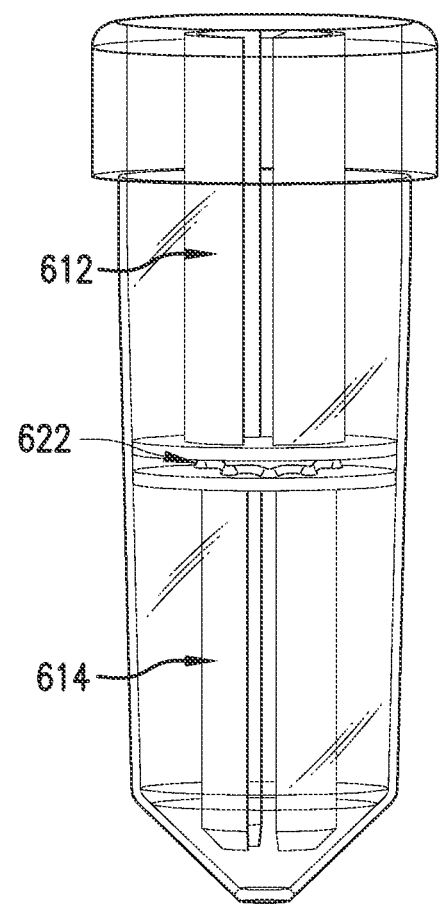
FIG. 12B is a schematic diagrams showing the assembled embodiment of FIG. 12A.

In an alternative embodiment, a singular elongate tubular body 610 can include scaling plungers 612 and 614 disposed therein, and a filter membrane 622 disposed between he plungers, as depicted in FIG. 12A-B. The plungers support the filter membrane 622 at a location suspended between the ends of the tubular body 610, e.g., at a midpoint of the tubular body 610, and have a radial flange circumscribing the plunger which seals off an upper and lower reservoir within the tubular body 610. This seal prohibits fluid transfer between reservoirs during centrifugation, thereby forcing all liquid to pass through the filter membrane 622. As described above, locating the filter membrane at the midpoint of the tubular body is advantageous in that it provides reservoirs of equivalent size and amounts of fluid contained therein. However, the plungers 612, 614 can be sized as so desired to position the filter membrane at any point along the tubular body 610.

Figure 13A:
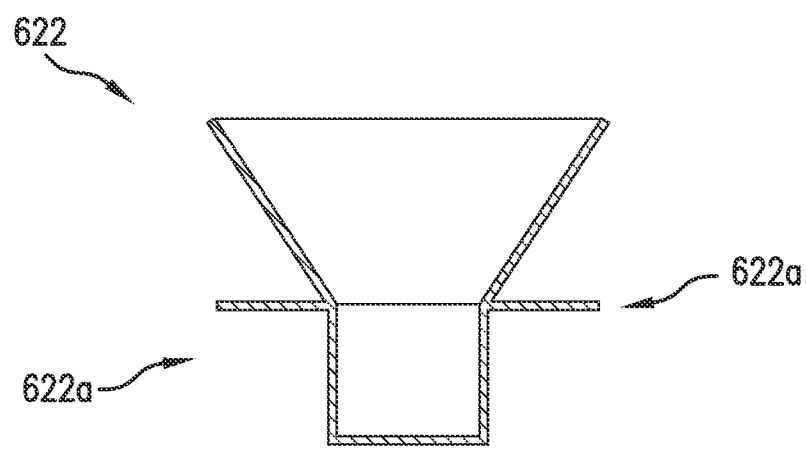
FIGS. 13A-D are cross-sectional diagrams of another embodiment of the filter membrane of the disclosed subject matter.
Figure 13B:
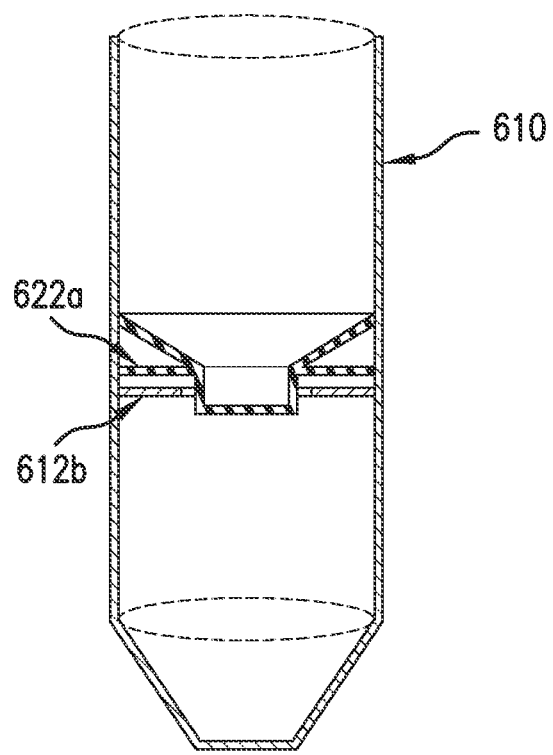
Figure 13C:
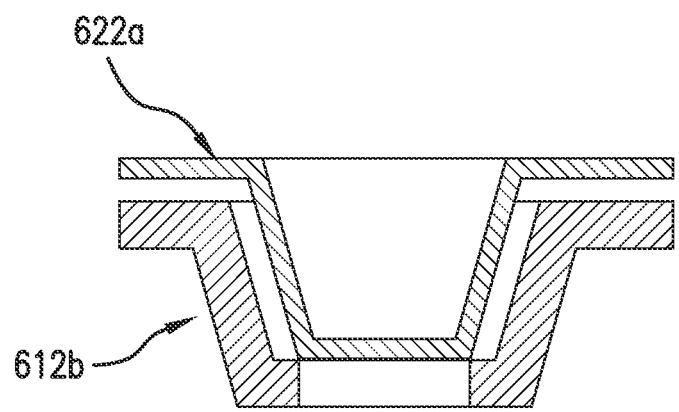

In some embodiments the filter membrane can include structural reinforcement features. In the exemplary embodiment shown in FIG. 13A, a bowl-like filter membrane 622 (shown in cross-sectional view) includes radially outwardly extending protrusions or shelves 622a that are sized to engage a corresponding shelf or lip in the elongate tube 610 which receives the filter membrane, as shown in FIG. 13B. These radially outwardly extending protrusions or shelves 622a strengthen the sidewalls of the filter membrane and absorb some of the forces generated during the centrifuge process. In some embodiments, the shelves 612b of the elongate tube member 610 are contoured to engage the filter membrane shelves 622a over a greater surface area (e.g., the sidewalls of the bowl-like filter membrane) as shown in FIG. 13C. This increased area of engagement between the filter membrane and the elongate tubular member provides additional support to the filter membrane during centrifuge process. Furthermore, the structural reinforcement features 622a and 612b allow for the filter membrane to be securely positioned within a single piece elongate tubular member 610. This can be advantageous in that it reduces the total number of parts as well as the assembly/disassembly steps required to carry out the method of the disclosed subject matter.

Figure 13D:
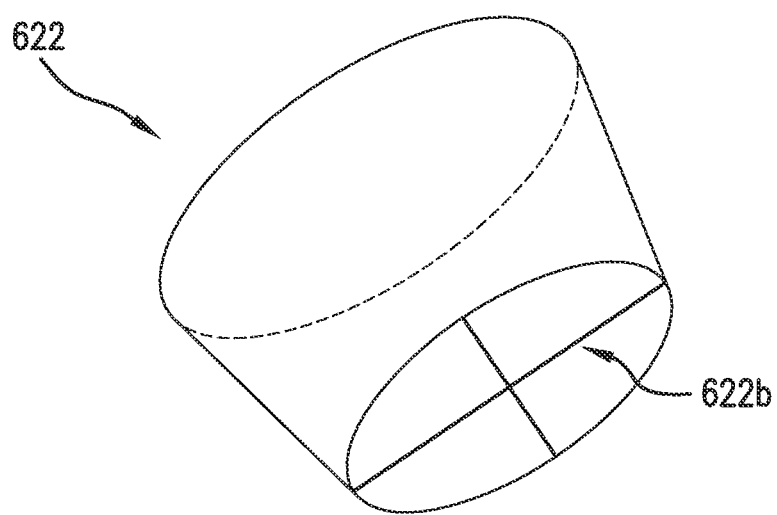

Additionally or alternatively, the structural reinforcement features can include struts 622b disposed at the bottom of the filter membrane which extend across the length, e.g., diameter, of the filter membrane 622, as shown in FIG. 13D. These struts 622b prevent the filter membrane from warping or breaking when exposed to forces associated with the centrifuge process. These structural reinforcement features disclosed herein can be formed integrally with the filter membrane, or alternatively formed as a separate insert that is positioned below the filter membrane.

Additionally, a handle (not shown) can be incorporated into the filter membrane which extends above the opening of the elongate tube member to allow the membrane to be easily removed. In this regard, the operator grasps the handle at a location which is spaced above the collected cell sample, thereby eliminating any risk of contamination or accidental loss of the sample. In some embodiments, the handle can extend radially outward through a slot formed in the tubular body, as described above and shown in FIG. 9D.

Figure 14C:
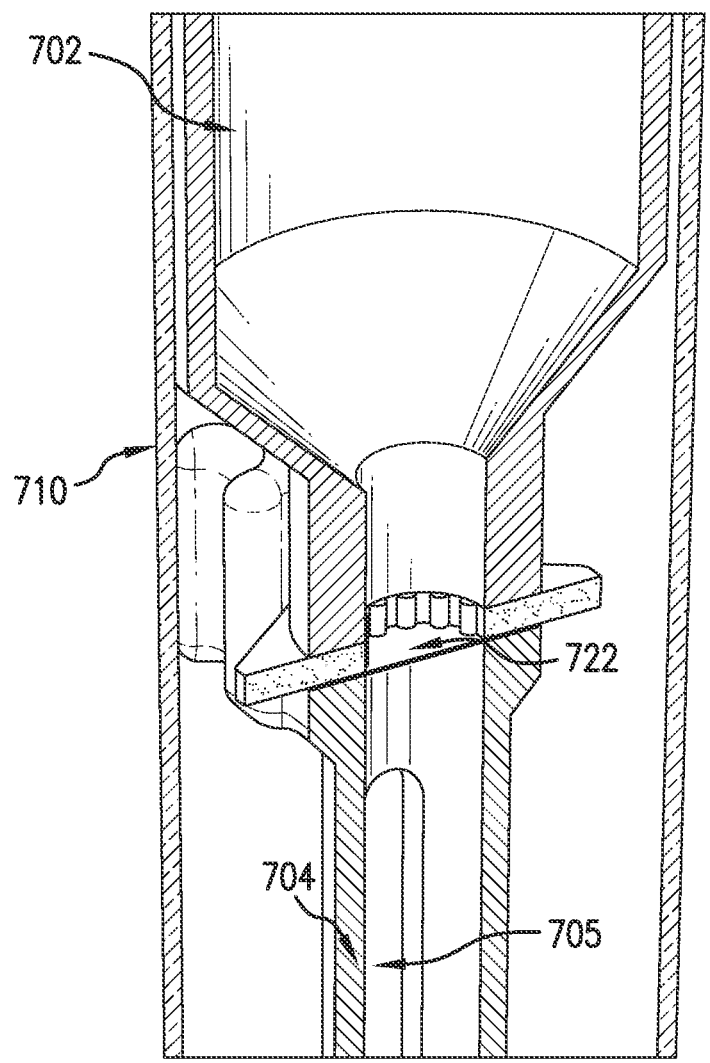
FIG. 14C is a cross-sectional view showing the assembled embodiment of FIG. 14B.

In an alternative exemplary embodiment, a sample loading chamber 702 and filter membrane 722 are disposed on a support post 704 and housed within a unitary elongate tubular body 710, as shown in FIGS. 14A-C. The support post 704 is disposed below the filter membrane and extends longitudinally to position the filter membrane 722 at a location suspended between the ends of the tube 710, e.g., at a midpoint of the tube 710. The filter membrane 722 can include a radially extending border portion, e.g., flange, which seals off an upper and lower reservoir within the elongate tubular member 710. This seal prohibits fluid transfer between reservoirs during centrifugation, thereby forcing all material to pass through the filter membrane. As described above, locating the filter membrane at the midpoint of the tube is advantageous in that such a configuration results in equivalent size reservoirs. However, alternative locations of the filter membrane are within the scope of the disclosed subject matter.

The support post 704 can include longitudinally extending slots or channels 705. These slots serve as passageways which allow for the liquid disposed below the filter membrane to freely move around within the lower reservoir formed during the centrifuge process to avoid localized pockets or cells of concentrated liquid. Additionally or alternatively, the slots can be configured as discontinuous local openings, e.g., circular apertures. An additional advantage of the embodiment depicted in FIGS. 14A-C is that it can be readily configured to fit existing centrifuge tubes, thus avoiding expensive or complex retrofit operations. In addition for allowing for passage of fluid, the slot 705 allows for deflection of the support post 704 to compensate and adjust for variances in length (e.g. due to manufacturing tolerances) of the various pieces upon assembly of the apparatus. That is, the components 702, 722, and 704 are positioned inside the tube 710 and compressed when the cap is attached at the top of the tube. The slot 705 provides a spring action which can bend to allow the filter membrane/assembly to be compressed for a range of height variations.

Figure 15:
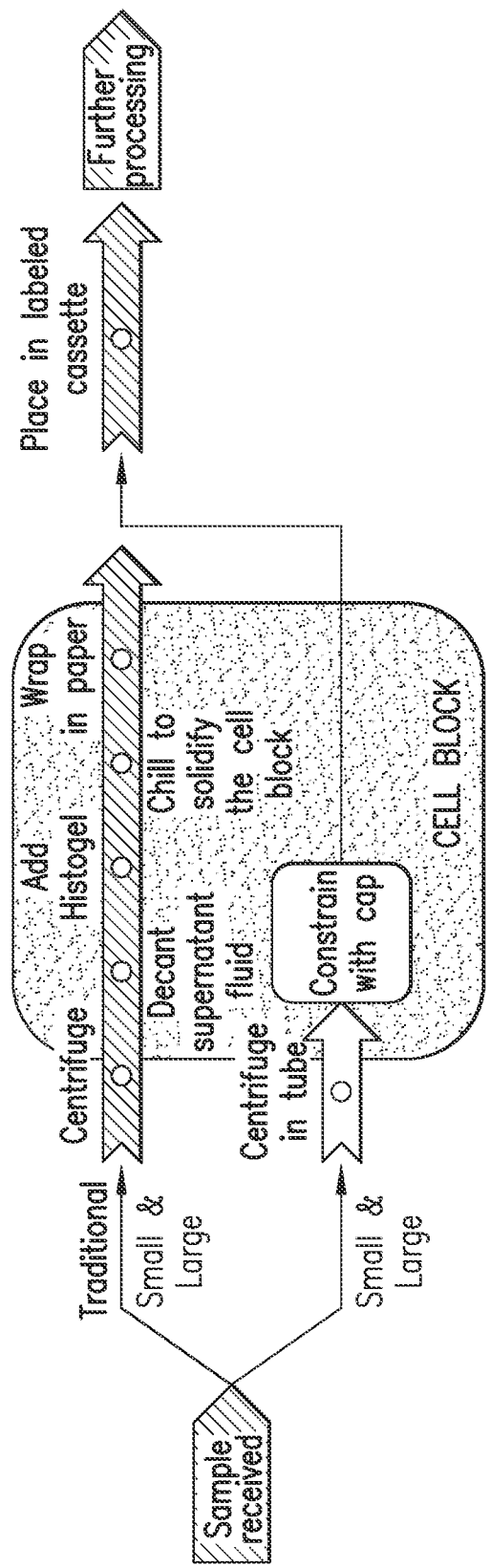
FIG. 15 is a flow diagram of the process of the disclosed subject matter.

In accordance with another aspect of the disclosed subject matter, the systems disclosed herein allow for an improved FNA processing protocol which reduces the number of steps of the presently disclosed subject matter (denoted by reference numeral 20) as compared to traditional prior art techniques (denoted by reference numeral 10), as shown in FIG. 15.

Figure 16:
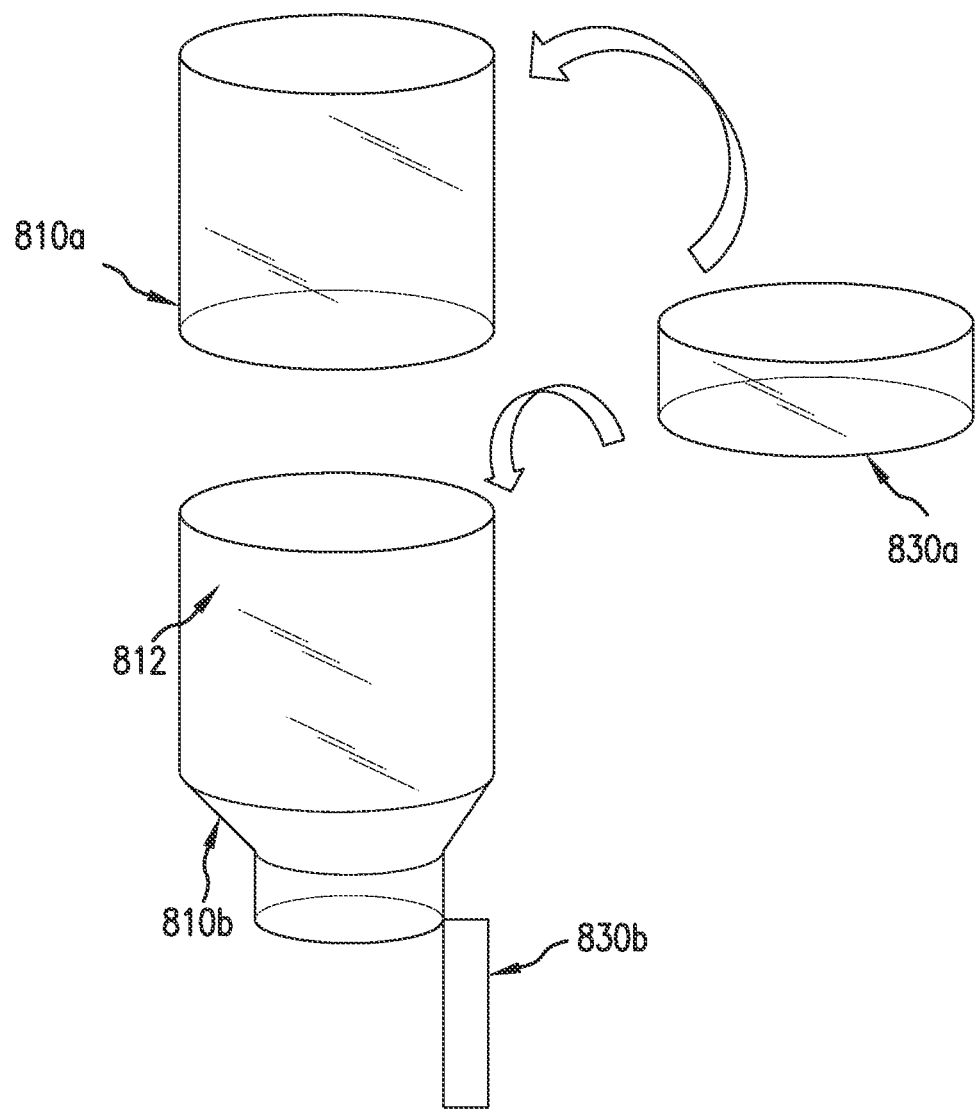
FIG. 16 is an exploded view of an alternative exemplary embodiment of the disclosed subject matter.

From a pathology perspective, physicians are typically interested in examining the cells collected by the filter membrane, whereas from a diagnostic, biochemical, and molecular perspective, physicians are typically interested in examining the liquid or "supernatant" which passes through filter membrane. Consequently, in some scenarios both portions of the sample (i.e. cell and supernatant) are retained and need to be sent to two different laboratories. Thus, and in accordance with another aspect of the disclosed subject matter, the filter membrane with the collected cell sample can be removed, while the supernatant is secured within the tube for parallel processing. In the exemplary embodiment illustrated in FIG. 16, after a centrifuge process is performed the sample cell is retained by filter membrane (not shown) to rest on shelves 812, and the fluid or supernatant is contained within lower tubular member 810b.

A first cap 830a is provided to engage with the top of either the elongate tubular member 810a (for scenarios in which it is desirable to remove the filter membrane and collected cell sample while packaging the fluid supernatant in the two tubes 810a, 810b together), or elongate tubular member 810b (for scenarios in which it is desirable to remove the filter membrane and collected cell sample while packaging the fluid supernatant in tube 810b alone). A second cap 830b is provided to engage with the bottom of elongate tubular member 810b. In some embodiments the second cap 830b is hingedly attached to the tubular member 810b and allowed to pivot between open and closed positions. This allows for rapid removal of the fluid in a controlled manner that is not obstructed by the filter assembly above.

The first cap 830a can be configured with both internal and external threads such that a single cap can be employed with a plurality of tube sizes (i.e., male engagement with smaller diameter tubes, and a female engagement with larger diameter tubes). It is to be understood that the disclosed cap arrangements can be employed on any of the disclosed tubular configurations (e.g., one piece, two-piece, telescopingly received, etc.) and for any desired size. Furthermore, in some embodiments, prior to use of the apparatus, the components of the disclosed subject matter are sized such that as the cap 830a is tightened on the tube a compressive force is applied to further compress the filter membrane to ensure a leak-tight seal is formed (between the filter membrane and interior surface of the tubular body) during the centrifuge process. Similarly, upon insertion of the filter assembly components within the tube(s), the user can compress the assembly such that the frictional forces retained between the filter assembly components and the tube sidewall creates a seal which allows a user to pour the contents into the tube without concern for unwanted leakage past the filter membrane prior to centrifuging.

Figure 17A:
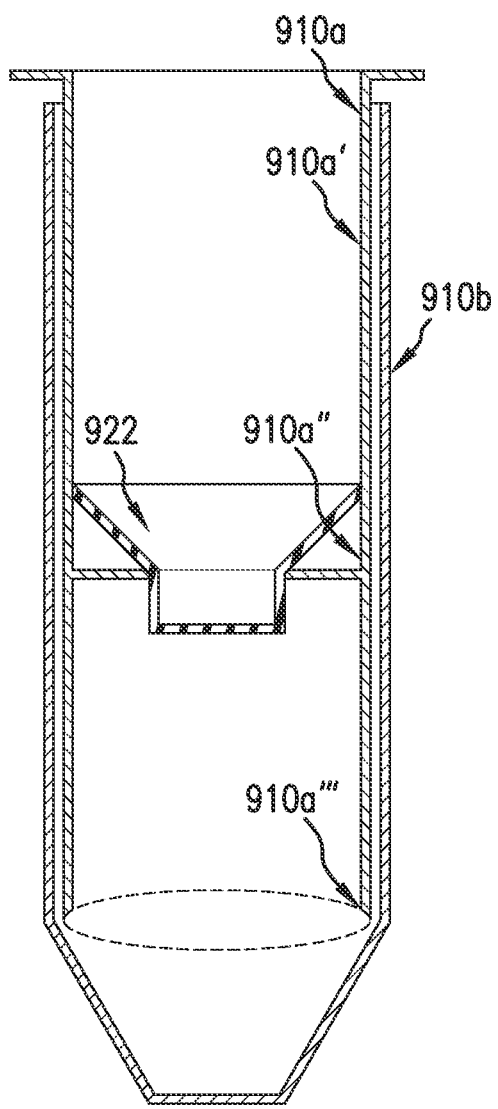
FIG. 17A is a schematic diagram of an alternative exemplary embodiment of the disclosed subject matter.
Figure 17B:
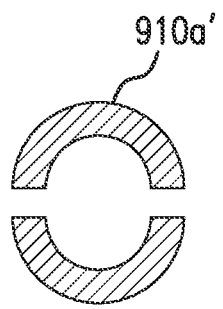
FIG. 17B-D are cross-sectional plan views showing the assembled embodiment of FIG. 17A.
Figure 17C:
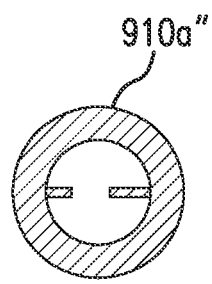
Figure 17D:
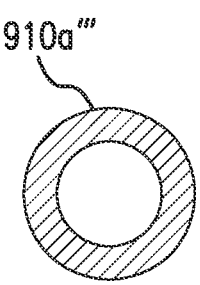

FIG. 17A depicts another exemplary embodiment of the disclosed subject matter in which the first elongate tubular body 910a is fully inserted within the second elongate tubular body 910b. The filter membrane is inserted within the first (or inner) elongate tubular body 910a and includes structural reinforcement members in the form of a outwardly protruding shelf to be received by corresponding inwardly protruding shelf of the first (or inner) elongate tubular body 910a. As described above, the first elongate tubular body 910a can include longitudinally extending slots formed in the sidewall of the tube. These slots extend from the location of the filter membrane retaining shelf (e.g., the midpoint of tube 910a) upwards to the top of the container. FIGS. 17B-D depict a top view of a cross-section of the first elongate tubular body 910a at the respective locations 910a', 910a'', and 910a''' along the length of the elongate tubular body as designated in FIG. 17A. The upwardly extending slots are advantageous in that they allow for a filter membrane to be easily placed and readily removed from within the first tube 910a by grabbing the filter membrane 922 from exterior of the elongate tubular body 910 (e.g., by the handles described above, if present) and sliding the filter membrane up and out of the tube 910a. An additional advantage of the embodiment depicted in FIGS. 17A-D is that it can be readily configured to fit existing centrifuge tubes, thus avoiding expensive or complex retrofit operations.

Figure 18:
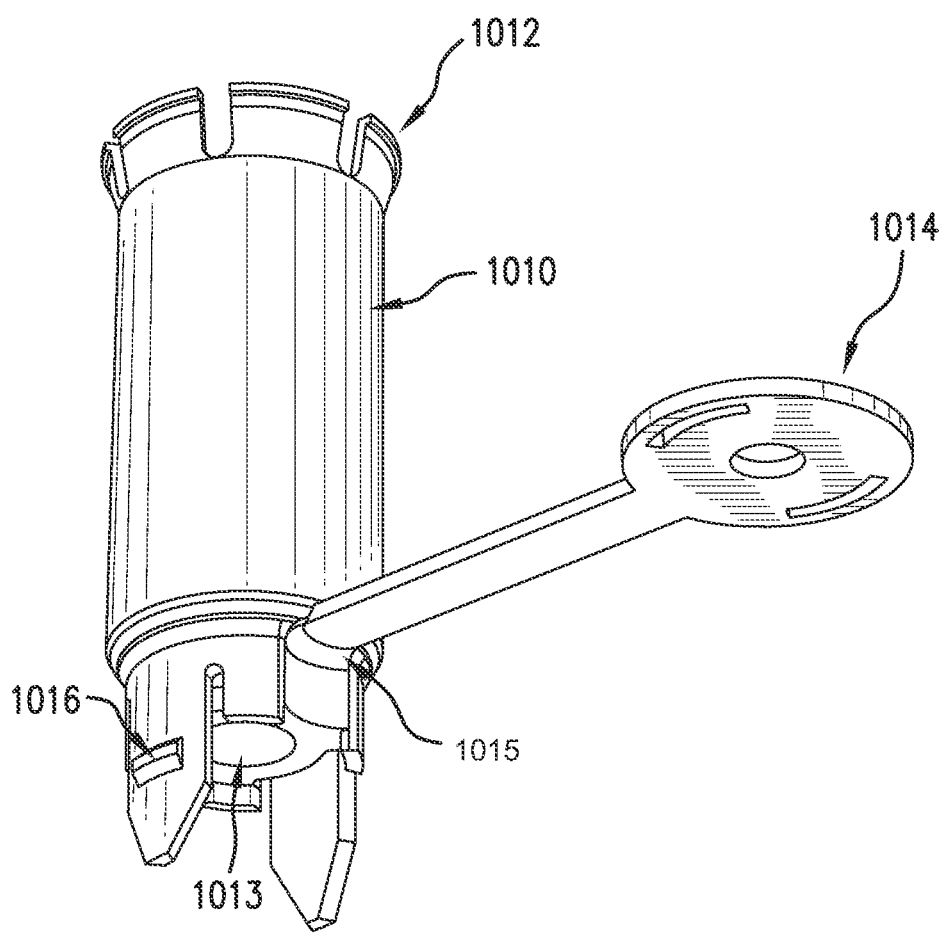
FIG. 18 is a schematic diagram of an alternative exemplary embodiment of the disclosed subject matter.

In another embodiment, and as depicted in FIG. 18, an elongate tubular body 1010 which is designed to be inserted within a second elongate tubular body (not shown). The elongate tubular body 1010 includes a proximal or top end having a structural retention feature 1012, (e.g., flange or ledge) configured to engage the top of the second elongate tubular body upon insertion therein. The structural retention feature 1012 can extend so as to curl or overlay a lip formed in the second elongate tubular body to provide a more secure union. At a distal or bottom end of the elongate tubular body 1010, a closing mechanism (e.g., cap) 1014 is hingedly attached at 1015 (e.g. by a living hinge) to the elongate tubular body 1010. Accordingly, the closing mechanism 1014 can pivot between open and closed positions. A filter membrane or assembly (not shown) can be positioned at the distal end 1013 of the elongate tubular body 1010 and securely retained in this position by rotating the closing mechanism 1014 from the open (as depicted in FIG. 18) to closed (not shown) positions. A locking mechanism (e.g., protrusion) 1016 can be included on the distal end of the elongate tubular body 1010 in order to secure the closing mechanism 1014 in the closed position and retain the filter membrane/assembly therein for commencement of a filtration process. In the embodiment depicted in FIG. 18, the closing mechanism 1014 includes slots for receiving in a snap-fit engagement the locking mechanism 1016. Upon completion of the filtration process, a user can squeeze the downwardly extending tabs of the elongate tubular body 1010 to cause deflection and release of the locking mechanism 1016 from the slots within the closing mechanism 1014.

Figure 19B:
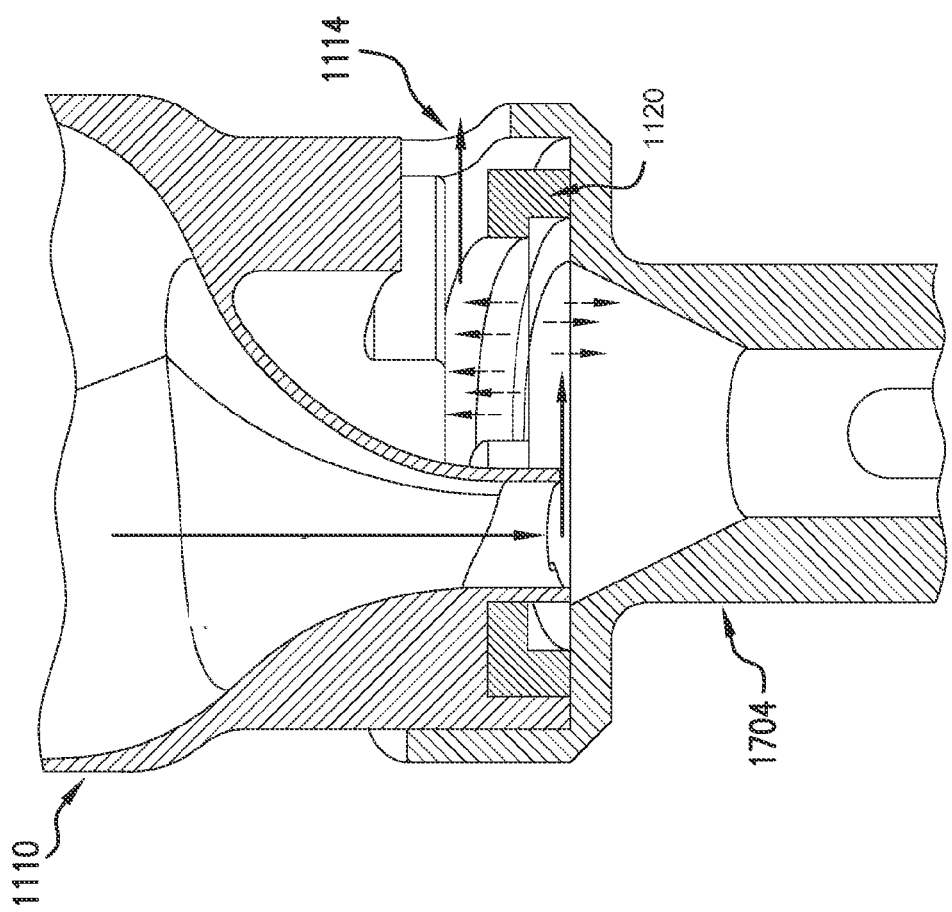
FIGS. 19A-B are schematic diagrams of an alternative exemplary embodiment of the disclosed subject matter, with FIG. 19B depicting a zoom-in view of a cross-sectional view.
Figure 19A:
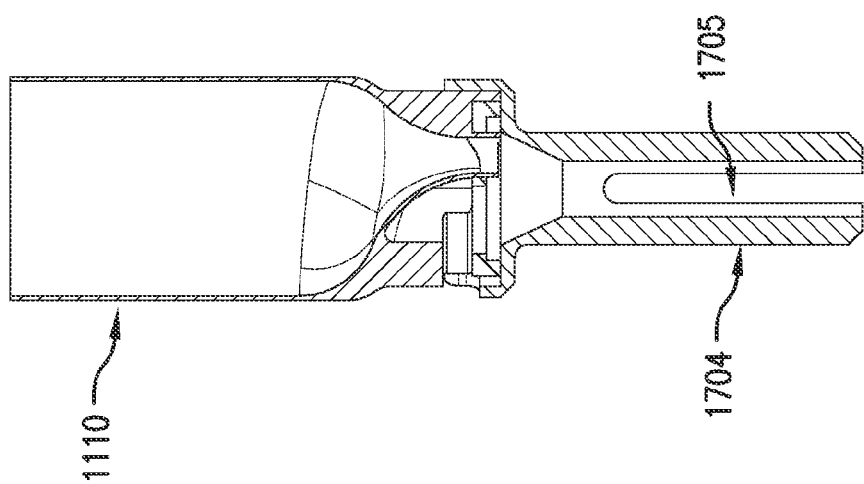
Figure 20A:
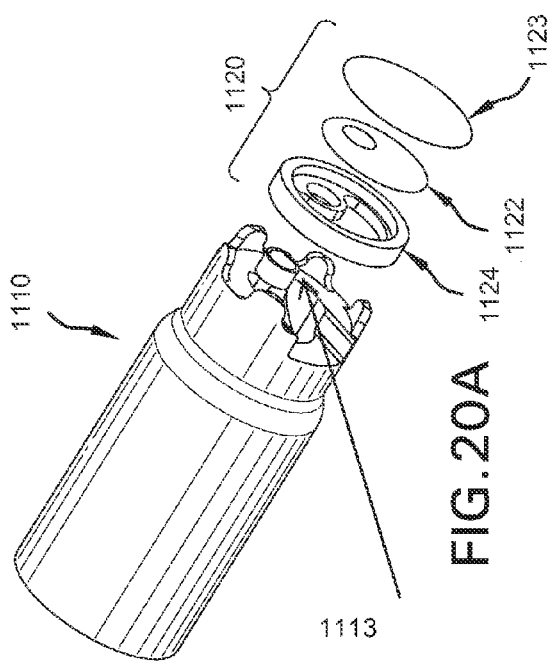
FIG. 20A-D are schematic diagrams of the embodiment of FIGS. 19A-B, with FIG. 20A depicting a exploded view, FIGS. 20B-C depicting partially assembled views, and FIG. 20D depicting a fully assembled view.
Figure 20B:
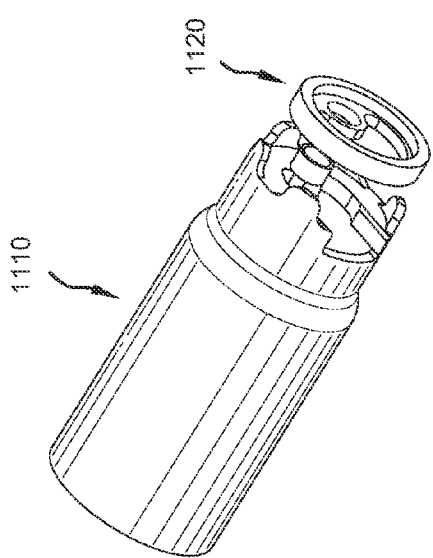
Figure 20C:
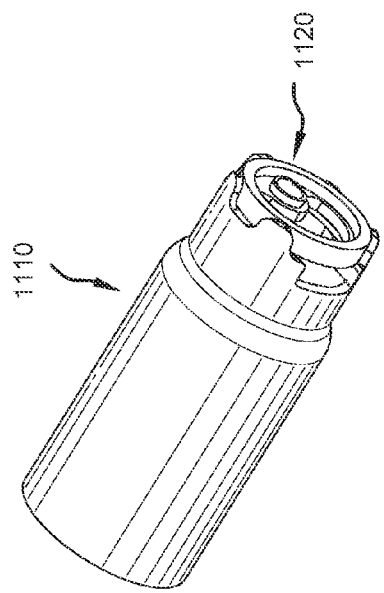
Figure 20D:
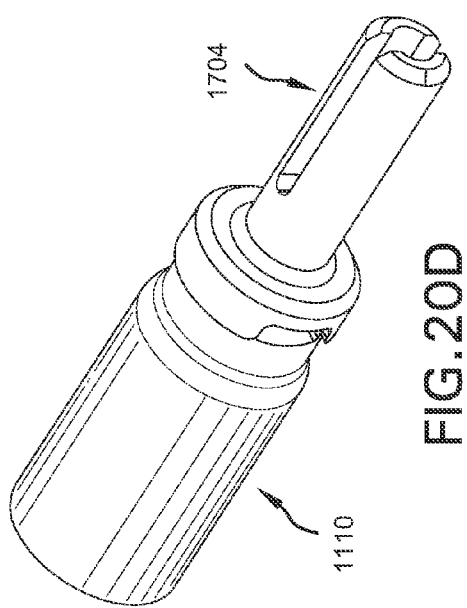

In yet another embodiment, an alternative geometry is provided which employs cross-flow filtration which increases the filtration surface area and thereby reduces the overall cycle time required for a desired amount of filtration, as well as minimizes clogging. The structure depicted in FIG. 19A-B includes a elongate tubular body 1110 and underlying support member 1704 which can be configured for assembly and placement within a second elongate tubular body (not shown). Also, the support member 1704 includes a slot or channel 1705, which functions similarly to the slot 705 disclosed above with respect to FIGS. 14A-C. The filter membrane 1120 (or assembly, if configured as discrete components) includes two filtration surfaces, i.e. upper surface 1122 and lower surface 1123 (see FIG. 20A). The upper filtration surface 1122 is sized such that it is received within the housing or border portion 1124. The lower filtration surface 1123 is sized such that it has an equivalent outer diameter as the housing 1124.

The elongate tubular body 1110 has an internal taper resulting in a reduced diameter (relative to the proximal opening or mouth) outlet 1112 which extends into the filtration space defined between the upper and lower surfaces of the filter membrane 1120. The outlet includes a non-planar surface 1113 at the opening, such as a notch or recess. Accordingly, only a portion of the outlet 1112 engages the lower filtration surface 1120, when assembled, resulting in a lateral port or recess which presents a path of least resistance for exiting fluid. Consequently, as fluid exits the outlet, the non-uniform surface at the outlet 1113 imparts a force on the exiting fluid which directs a portion of the flow in a transverse or tangential direction, across the filter surface (as indicated by the arrows in FIG. 19B). The elongate tubular body 110, and/or the underlying support member 1704, also include a side port 1114 which allows fluid to exit the apparatus and enter the main centrifuge tube (not shown).

Figure 22:
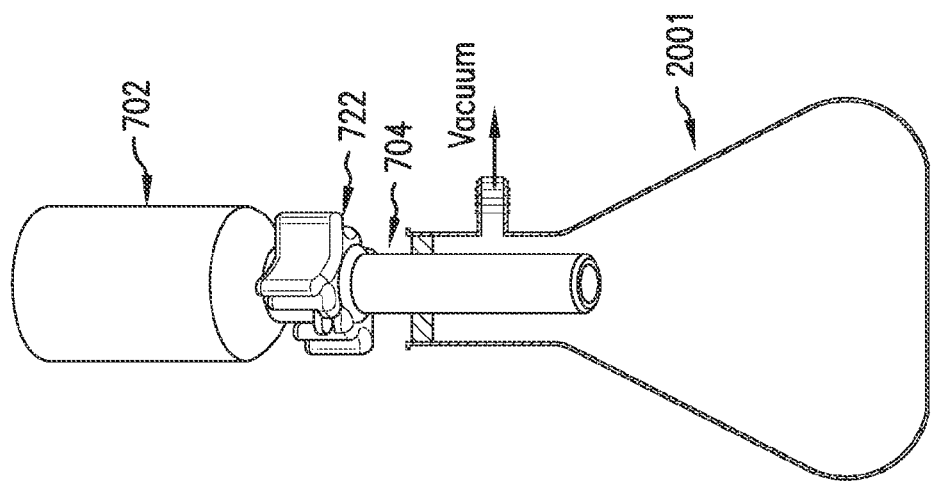
FIGS. 21-22 are schematic diagrams of an alternative exemplary embodiment of the disclosed subject matter depicting vacuum mechanisms.
Figure 21:
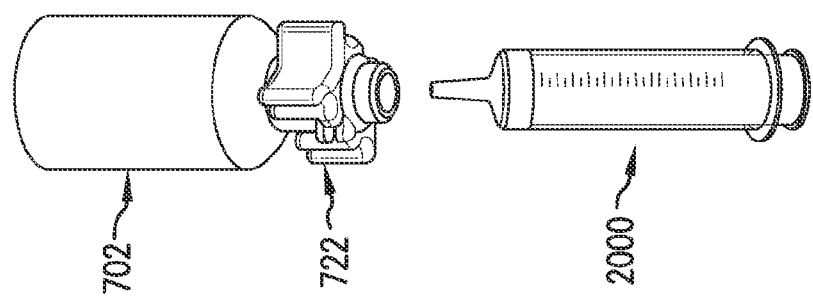

In accordance with another aspect of the disclosed subject matter, and as an alternative to conventional centrifuging processes, the filtration force employed in concert with the apparatus disclosed herein can be provided by a suction force. For purposes of illustration and not limitation, FIGS. 21-22 illustrate some embodiments wherein the driving force is provided via a syringe (FIG. 21) or a vacuum source (FIG. 22). For example, the support member 722 (as previously disclosed with respect to FIGS. 14A-C) can be configured with a tapered opening to sealingly couple with an external syringe 2000. The user can then pull back on the syringe plunger to draw the fluid from the elongate tubular body 702, through the filter membrane 722 and into the barrel of the syringe. Similarly, and as depicted in FIG. 22, an external vacuum source can be coupled to the support member 704 and activated to draw the fluid from the elongate tubular body 702, through the filter membrane 722 and into a receptacle or reservoir 2001 of the vacuum.

The various components identified in these embodiments can be discrete members which are assembled in such a manner that each component is readily removable (i.e. detachable without breaking). Such a construction is advantageous in that it allows for rapid assembly in preparation for the centrifuge process, and subsequent disassembly in order to rapidly access the filter membrane and the collected cell sample disposed thereon. This readily removable feature avoids risk of contamination presented by permanent or welded connections which require fracturing or breaking of components and seals, and the debris associated with such efforts, to access the filter and collected cell sample.

In some embodiments, the cell block apparatus and components are color coded. For example, the filter assembly can be color coded so that the laboratory personnel or the clinicians can easily identify the type of sample in the filter assembly. For the purpose of illustration and not limitation, the material of the filter assembly can be purple to denote a liver sample, and blue to denote a lung sample. The color codes of the filter assembly or the elongate tubular body can be coordinated with the compressive cover to function as indicia.

It is understood that the subject matter described herein is not limited to particular embodiments described, as such may, of course, vary. For example, the exemplary embodiments describe above are not limited to fine needle aspiration applications. Instead the disclosed subject matter is applicable to additional clinical settings such as processing small surgical biopsies (less than 2 cm), in research laboratories for isolating cells from bone marrow diluted by blood, analyzing small samples of engineered tissues, and purifying cells in a spin column. Accordingly, nothing contained in the Abstract or the Summary should be understood as limiting the scope of the disclosure. It is also understood that the terminology used herein is for the purpose of describing particular embodiments only, and is not intended to be limiting. Where a range of values is provided, it is understood that each intervening value between the upper and lower limit of that range and any other stated or intervening value in that stated range, is encompassed within the disclosed subject matter.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

As used herein and in the appended claims, the singular forms "a," "an," and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A medical apparatus comprising:
    a first elongate tubular body member having a proximal end and a distal end defining an interior space therebetween, and means for engaging a filter member assembly unit,
    a filter assembly unit comprising a bottom surface including a porous membrane and a base member having a body circumferentially surrounding the porous membrane and having upwardly extending sidewalls such that the bottom surface and upwardly extending sidewalls define a receptacle for collecting a biological sample, the filter assembly unit further including a structural reinforcement member for removably attaching to the engaging means of the first elongate tubular body member,
    wherein the base member consists essentially of paraffin material and the entire filter assembly unit is sliceable into sections suitable for mounting on a slide for microscopy.

2. The medical apparatus of claim 1, wherein the filter assembly unit is engaged to the distal end of the first elongate tubular body member.

3. The medical apparatus of claim 1, wherein the means for physically engaging the filter member assembly unit includes a platform disposed at the distal end of the first elongate body member.

4. The medical apparatus of claim 1, wherein the structural reinforcement member removably attaches the filter assembly between the proximal and distal ends of the first elongate tubular body.

5. The medical apparatus of claim 1, wherein the structural reinforcement member includes a protrusion configured to engage a shelf extending from a surface of the first elongate tubular body.

6. The medical apparatus of claim 1, wherein the filter assembly includes a plurality of peaks and valleys extending around at least a portion of its circumference.

7. The medical apparatus of claim 1, wherein the porous membrane is centrally disposed in the receptacle.

8. The medical apparatus of claim 1, wherein the filter assembly includes recesses distributed about the base member.

9. The medical apparatus of claim 1, wherein the filter assembly includes indicia for orientation of a collected biological sample.

10. The medical apparatus of claim 1, further comprising a second elongate tubular body sized to receive at least a portion of the first elongate tubular body.

11. The medical apparatus of claim 10, wherein the first elongate tubular member includes a platform to attach to the filter assembly and a circumscribing shelf for attaching the first elongate tubular body to the second elongate tubular member.

12. The medical apparatus of claim 1, further comprising a cover pivotably connected to the distal end of the first elongate tubular member.

13. The medical apparatus of claim 1, wherein the proximal end of the first elongate tubular body is open and the apparatus further includes a lid sized to close an opening at the proximal end of the elongate tubular member, the lid formed of material capable of self-sealing after puncture by a needle.

14. A medical apparatus comprising:
a first elongate tubular body member having a proximal end and a distal end defining an interior space therebetween, and means for engaging a filter member assembly unit;
a second elongate tubular body member having a proximal end and a distal end defining an interior space therebetween sized to receive the first elongate tubular body, and
a filter assembly comprising a unitary body having a bottom surface and upwardly extending sidewalls to define a receptacle suitable to hold a biological sample, and a structural reinforcement member for removably attaching the filter assembly to the engaging means of the first elongate tubular member,
wherein the upwardly extending sidewalls consist essentially of paraffin material and the assembly is sliceable into sections suitable for mounting on a slide.

15. The medical apparatus of claim 14, wherein the receptacle contains a cell block.

16. The medical apparatus of claim 15, wherein the entire filter assembly is sliceable without contaminating the cell block.

17. The medical apparatus of claim 14, wherein the structural reinforcement member includes threads to engage the distal end of the first elongate tubular member.

18. The medical apparatus of claim 14, wherein the structural reinforcement member includes a protrusion to engage the distal end of the first elongate tubular member.

19. The medical apparatus of claim 14, wherein the structural reinforcement member engages a shelf disposed in the first elongate tubular body.

20. A filter assembly for preparing cells block comprising:
a unitary body including a non-porous base member having an upwardly extending wall bordering a membrane having pores between about 0.4 µm to about 5 µm, the base member and porous membrane defining a receptacle suitable for collecting and processing a biological sample into a cell block, the unitary body further including at least one structural reinforcement member such that the filter assembly can removably attach to a tubular body member,
wherein the non-porous base member consists essentially of paraffin material and the filter assembly sliceable into sections suitable for mounting on a slide for microscopy while holding a cell block.

21. The filter assembly of claim 20, wherein the filter assembly has an outer surface including alternating peaks and valleys around the periphery of the unitary body.

22. The filter assembly of claim 20, wherein the filter assembly further includes a compressive cover for enclosing the receptacle defined by the base member and porous membrane.

23. The filter assembly of claim 22, further including a cell block disposed in the receptacle.

24. The filter assembly of claim 20, wherein the filter assembly is engaged to an elongate tubular body member.

25. The filter assembly of claim 24, wherein the engaged elongate tubular body member and filter assembly are disposed within a centrifuge tube.

26. The medical apparatus of claim 14, wherein the first elongate tubular body member is engaged to the filter assembly, and further wherein the first elongate tubular body member and engaged filter assembly is disposed within the second tubular body member.

* * * * *